(12) United States Patent
Labhasetwar et al.

(10) Patent No.: US 11,013,817 B2
(45) Date of Patent: May 25, 2021

(54) NANOPARTICLES FOR DRUG DELIVERY TO TREAT BONE DISEASE

(71) Applicant: The Cleveland Clinic Foundation, Cleveland, OH (US)

(72) Inventors: Vinod Labhasetwar, Cleveland, OH (US); Isaac M. Adjei, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 16/092,063

(22) PCT Filed: Apr. 7, 2017

(86) PCT No.: PCT/US2017/026599
§ 371 (c)(1),
(2) Date: Oct. 8, 2018

(87) PCT Pub. No.: WO2017/177134
PCT Pub. Date: Oct. 12, 2017

(65) Prior Publication Data
US 2019/0307896 A1    Oct. 10, 2019

Related U.S. Application Data

(60) Provisional application No. 62/319,926, filed on Apr. 8, 2016.

(51) Int. Cl.
*A61P 35/00* (2006.01)
*A61P 19/10* (2006.01)
(Continued)

(52) U.S. Cl.
CPC ........ *A61K 47/6937* (2017.08); *A61K 9/5138* (2013.01); *A61K 9/5153* (2013.01);
(Continued)

(58) Field of Classification Search
CPC .. A61K 31/74; A61K 47/6937; A61K 9/5138; A61K 9/5153; A61P 19/10; A61P 35/00; B82Y 5/00
See application file for complete search history.

(56) References Cited

U.S. PATENT DOCUMENTS

2009/0061010 A1   3/2009   Zale et al.
2010/0266491 A1   10/2010  Farokhzad et al.
(Continued)

FOREIGN PATENT DOCUMENTS

WO    WO 2015/134032    9/2015
WO    WO 2015/138925    9/2015

OTHER PUBLICATIONS

Danhier et al. (Journal of Controlled Release 2009;133:11-17). (Year: 2009).*
(Continued)

*Primary Examiner* — Ernst V Arnold
(74) *Attorney, Agent, or Firm* — Casimir Jones, S.C.; Jason R. Bond

(57) ABSTRACT

Provided herein are compositions, systems, kits, and methods for treating cancer in at least one bone of a subject using nanoparticles encapsulating, or conjugated to, an anti-cancer agent. In other embodiments, provided herein are composition, systems, kits, and methods for treating a bone disease (e.g., osteoporosis) in a subject using nanoparticle encapsulating, or conjugated to, a RANKL inhibitor. The nanoparticle are, in certain embodiments, neutral or nearly neutral in charge (e.g., zeta potential between −5 and +5 mV) and less than 250 nm in diameter on average (e.g. have an average diameter between 100 and 200 nm).

6 Claims, 14 Drawing Sheets

(51) Int. Cl.
A61K 31/74 (2006.01)
B82Y 5/00 (2011.01)
A61K 47/69 (2017.01)
A61K 9/51 (2006.01)
C07K 16/28 (2006.01)

(52) U.S. Cl.
CPC ............ A61K 31/74 (2013.01); A61P 19/10 (2018.01); A61P 35/00 (2018.01); C07K 16/2878 (2013.01); B82Y 5/00 (2013.01)

(56) References Cited

U.S. PATENT DOCUMENTS

2015/0125391 A1* 5/2015 Swami ............... A61K 38/1875
424/9.1
2016/0032400 A1* 2/2016 Gomis ............. G01N 33/57407
424/135.1

OTHER PUBLICATIONS

Ganellin et al. (Introduction to Biological and Small Molecule Drug Research and Development: Theory and Case Studies. 2013 Academic Press p. 187) (Year: 2013).*
Atkins et al. (Bone 2001;38(4):370-377). (Year: 2001).*
Ganju et al. (Drug Resist Updat2014;17(0):13-23) (Year: 2014).*
Keum et al. (International Journal of Nanomedicine 2011;6:2225-2234) (Year: 2011).*
Helo et al. (Prostate Cancer and Prostateic Diseases 2012;15:231-236). (Year: 2012).*
Adjei et al., Heterogeneity in nanoparticles influences biodistribution and targeting. Nanomedicine (Lond). Feb. 2014;9(2):267-78.
Ang et al., Paclitaxel inhibits osteoclast formation and bone resorption via influencing mitotic cell cycle arrest and RANKL-induced activation of NF-κB and ERK. J Cell Biochem. Mar. 2012;113(3):946-55.
Arvizo et al.,Modulating pharmacokinetics, tumor uptake and biodistribution by engineered nanoparticles. PLoS One. 2011;6(9):e24374.
Asati et al., Surface-charge-dependent cell localization and cytotoxicity of cerium oxide nanoparticles. ACS Nano. Sep. 28, 2010;4(9):5321-31.
Blanco et al., Principles of nanoparticle design for overcoming biological barriers to drug delivery. Nat Biotechnol. Sep. 2015;33(9):941-51.
Brannon-Peppas et al., Nanoparticle and targeted systems for cancer therapy. Adv Drug Deliv Rev. Sep. 22, 2004;56(11):1649-59.
Casas et al., Denosumab for the treatment of bone metastases in advanced breast cancer. Breast. Oct. 2013;22(5):585-92.
Coleman, Metastatic bone disease: clinical features, pathophysiology and treatment strategies. Cancer Treat Rev. Jun. 2001;27(3):165-76.
Davda et al., Characterization of nanoparticle uptake by endothelial cells. Int J Pharm. Feb. 21, 2002;233(1-2):51-9.
Davda et al., Sustained proangiogenic activity of vascular endothelial growth factor following encapsulation in nanoparticles. Journal of Biomedical Nanotechnology 2005;1:74-82.
Davis et al., Nanoparticle therapeutics: an emerging treatment modality for cancer. Nat Rev Drug Discov. 2008 Sep;7(9):771-82.
Drooger et al., Denosumab in breast cancer treatment. Eur J Pharmacol. Oct. 5, 2013;717(1-3):12-9.
El-Mabhouh, et al., A conjugate of gemcitabine with bisphosphonate (Gem/BP) shows potential as a targeted bone-specific therapeutic agent in an animal model of human breast cancer bone metastases. Oncol Res. 2011;19(6):287-95.
Farokhzad et al, Targeted nanoparticle-aptamer bioconjugates for cancer chemotherapy in vivo. Proc Natl Acad Sci U S A. Apr. 18, 2006;103(16):6315-20.

Gaumet et al., Nanoparticles for drug delivery: the need for precision in reporting particle size parameters. Eur J Pharm Biopharm. May 2008;69(1):1-9.
Hatakeyama et al., A multifunctional envelope type nano device (MEND) for gene delivery to tumours based on the EPR effect: a strategy for overcoming the PEG dilemma. Adv Drug Deliv Rev. Mar. 18, 2011;63(3):152-60.
Hirabayashi et al., Bone-specific drug delivery systems: approaches via chemical modification of bone-seeking agents. Clin Pharmacokinet. 2003;42(15):1319-30.
Hirsch et al., Surface charge of polymer coated SPIONs influences the serum protein adsorption, colloidal stability and subsequent cell interaction in vitro. Nanoscale. May 7, 2013;5(9):3723-32.
Hrkach et al., Preclinical development and clinical translation of a PSMA-targeted docetaxel nanoparticle with a differentiated pharmacological profile. Sci Transl Med. Apr. 4, 2012;4(128):128ra39.
Kakinoki et al., Synthesis and evaluation of water-soluble poly(vinyl alcohol)-paclitaxel conjugate as a macromolecular prodrug. Biol Pharm Bull. May 2008;31(5):963-9.
Kalaria et al., Design of biodegradable nanoparticles for oral delivery of doxorubicin: in vivo pharmacokinetics and toxicity studies in rats. Pharm Res. Mar. 2009;26(3):492-501.
Keller et al., Prostate cancer bone metastases promote both osteolytic and osteoblastic activity. J Cell Biochem. Mar. 1, 2004;91(4):718-29.
Kolate et al., PEG—A versatile conjugating ligand for drugs and drug delivery systems. J Control Release. Oct. 28, 2014;192:67-81.
Kwon, et al., Analysis on the current status of targeted drug delivery to tumors. J Control Release. Dec. 10, 2012;164(2):108-14.
Liu et al., Mapping microclimate pH distribution inside protein-encapsulated PLGA microspheres using confocal laser scanning microscopy. Mol Pharm. May 7, 2012;9(5):1342-50.
Mann, et al., E-selectin-targeted porous silicon particle for nanoparticle delivery to the bone marrow. Adv Mater. Sep. 22, 2011;23(36):H278-82.
Miller et al., RANK ligand inhibition plus docetaxel improves survival and reduces tumor burden in a murine model of prostate cancer bone metastasis. Mol Cancer Ther. Jul. 2008;7(7):2160-9.
Moghimi, Exploiting bone marrow microvascular structure for drug delivery and future therapies. Adv Drug Deliv Rev 1995; 17:61-73.
Nangia et al., Denosumab for treatment of breast cancer bone metastases and beyond. Expert Opin Biol Ther. Apr. 2012;12(4):491-501.
Oh, et al., Cellular uptake and fate of PEGylated gold nanoparticles is dependent on both cell-penetration peptides and particle size. ACS Nano. Aug. 23, 2011;5(8):6434-48.
Owens et al., Opsonization, biodistribution, and pharmacokinetics of polymeric nanoparticles. Int J Pharm. Jan. 3, 2006;307(1):93-102.
Panyam et al., Polymer degradation and in vitro release of a model protein from poly(D,L-lactide-co-glycolide) nano- and microparticles. J Control Release. Sep. 19, 2003;92(1-2):173-87.
Panyam, et al., Rapid endo-lysosomal escape of poly(DL-lactide-co-glycolide) nanoparticles: implications for drug and gene delivery. FASEB J. Aug. 2002;16(10):1217-26.
Panyam, et al., Solid-state solubility influences encapsulation and release of hydrophobic drugs from PLGA/PLA nanoparticles. J Pharm Sci. Jul. 2004;93(7):1804-14.
Panyam, et al.,Dynamics of endocytosis and exocytosis of poly(D,L-lactide-co-glycolide) nanoparticles in vascular smooth muscle cells. Pharm Res. Feb. 2003;20(2):212-20.
Qaddoumi et al., Clathrin and caveolin-1 expression in primary pigmented rabbit conjunctival epithelial cells: role in PLGA nanoparticle endocytosis. Mol Vis. Oct. 15, 2003;9:559-68.
Ramanlal Chaudhari et al., Bone metastasis targeting: a novel approach to reach bone using Zoledronate anchored PLGA nanoparticle as carrier system loaded with Docetaxel. J Control Release. Mar. 28, 2012;158(3):470-8.
Sahoo et al., JResidual polyvinyl alcohol associated with poly (D,L-lactide-co-glycolide) nanoparticles affects their physical properties and cellular uptake. J Control Release. Jul. 18, 2002;82(1):105-14.

(56) References Cited

OTHER PUBLICATIONS

Sarin, Physiologic upper limits of pore size of different blood capillary types and another perspective on the dual pore theory of microvascular permeability. J Angiogenes Res. Aug. 11, 2010;2:14.

Schroeder et al., Treating metastatic cancer with nanotechnology. Nat Rev Cancer. Dec. 23, 2011;12(1):39-5.

Souris et al., Surface charge-mediated rapid hepatobiliary excretion of mesoporous silica nanoparticles. Biomaterials. Jul. 2010;31(21):5564-7.

Swami et al., Engineered nanomedicine for myeloma and bone microenvironment targeting. Proc Natl Acad Sci U S A. Jul. 15, 2014;111(28):10287-92.

Tabata et al., Tumor accumulation of poly(vinyl alcohol) of different sizes after intravenous injection. J Control Release. Jan. 2, 1998;50(1-3):123-33.

Thamake et al., Alendronate coated poly-lactic-co-glycolic acid (PLGA) nanoparticles for active targeting of metastatic breast cancer.Biomaterials. Oct. 2012;33(29):7164-73.

Tsourdi et al., Denosumab for bone diseases: translating bone biology into targeted therapy. Eur J Endocrinol. Dec. 2011;165(6):833-40.

Uehara et al., Induction of retinol-binding protein 4 and placenta-specific 8 expression in human prostate cancer cells remaining in bone following osteolytic tumor growth inhibition by osteoprotegerin. Int J Oncol. Aug. 2013;43(2):365-74.

Verhoef et al., Questioning the use of PEGylation for drug delivery. Drug Deliv Transl Res. Dec. 2013;3(6):499-503.

Wang et al., Bisphosphonate-coated BSA nanoparticles lack bone targeting after systemic administration. J Drug Target. Sep. 2010;18(8):611-26.

Yamaoka et al., Comparison of body distribution of poly(vinyl alcohol) with other water-soluble polymers after intravenous administration. J Pharm Pharmacol. Jun. 1995;47(6):479-86.

Yuasa et al., Denosumab: a new option in the treatment of bone metastases from urological cancers. Onco Targets Ther. 2012;5:221-9.

Extended European Search Report for EP17779909.5, dated Nov. 18, 2019, 8 pages.

International Search Report and Written Opinion for PCT/US2017/026599, dated Jul. 14, 2017, 12 pages.

* cited by examiner

NANOPARTICLES FOR DRUG DELIVERY TO TREAT BONE DISEASE

The present application claims priority to U.S. Provisional application Ser. No. 62/319,926, filed Apr. 8, 2016, which is herein incorporated by reference in its entirety.

This invention was made with government support under RO1 CA206189, 1R01CA149359, and 1R01EB003975 awarded by the National Institutes of Health. The government has certain rights in the invention.

FIELD

Provided herein are compositions, systems, kits, and methods for treating cancer in at least one bone of a subject using nanoparticles encapsulating, or conjugated to, an anti-cancer agent. In other embodiments, provided herein are composition, systems, kits, and methods for treating a bone disease (e.g., osteoporosis) in a subject using nanoparticle encapsulating, or conjugated to, a RANKL inhibitor. The nanoparticle are, in certain embodiments, neutral or nearly neutral in charge (e.g., zeta potential between −5 and +5 mV) and less than 250 nm in diameter on average (e.g. have an average diameter between 100 and 200 nm).

BACKGROUND

Bone is a common site for metastasis in a number of human cancers (e.g., breast and prostate), in large part because of the relatively slow blood flow in bone marrow and the presence of adhesion receptors on bone marrow capillary endothelial cells that support cancer cell localization in the bone. These characteristics, together with the fact that bone marrow is an environment rich in growth factors and cytokines, all promote progression of bone metastasis [1, 2]. Among cancers that metastasize to bone, prostate cancer presents with a significantly high incidence: ~70-80% of patients develop bone metastases. The 5-year survival rate of patients with bone metastases is very low compared with those in whom the disease is localized (20% vs. 100%). As with prostate cancer, the majority of patients with advanced-stage breast cancer show evidence of skeletal metastases by the time of their death [3]. The consequences of bone metastasis are often devastating; it affects bone remodeling, causes bone pain, fractures and nerve compression, and in prostatic disease is the major cause of prostate cancer-related morbidity and mortality [4]. Since bone is less highly perfused than soft-tissue organs (7% of cardiac output goes to bone vs. 30% to liver) [5], intravenously administered anticancer chemotherapeutics do not achieve enough of a therapeutic dose at bone metastatic sites to suppress tumor growth. A major fraction of the administered drug is either excreted and/or metabolized, often via hepatic processes; or may accumulate in other, more highly perfused body compartments or tissues prior to reaching the marrow in sufficient doses.

To overcome this challenge, such approaches as conjugating anticancer drugs [6] or drug-loaded nanoparticles (NPs) to bone-seeking agents (e.g., bisphosphonates [7], tetracycline [8], or E-selectin [overexpressed in bone marrow endothelium] [9]) have been investigated, but these remain inefficient. For example, Wang et al. [10] found that bisphosphonate-conjugated to NPs made with bovine serum albumin did not target bone in vivo, despite in vitro results showing that they had significantly higher affinity than unconjugated NPs to hydroxyapatite, a major component of bone. In a recent study in a bone metastasis model of myeloma, Swami et al. [11] found no significant differences in the efficacy (bone loss, tumor burden, and survival) of alendronate (bisphosphonate)-conjugated NPs loaded with the proteasome inhibitor bortezomib compared with unconjugated NPs or drug alone. It is now increasingly recognized that for cancer chemotherapy to succeed, effective treatment of metastatic and advanced-stage tumors is critical.

SUMMARY

Provided herein are compositions, systems, kits, and methods for treating cancer in at least one bone of a subject using nanoparticles encapsulating, or conjugated to, an anti-cancer agent. In other embodiments, provided herein are composition, systems, kits, and methods for treating a bone disease (e.g., osteoporosis) in a subject using nanoparticle encapsulating, or conjugated to, a RANKL (receptor activator of nuclear factor-kappa B ligand) inhibitor. The nanoparticle are, in certain embodiments, neutral or nearly neutral in charge (e.g., zeta potential between −5 and +5 mV) and less than 250 nm in diameter on average (e.g. have an average diameter between 100 and 200 nm).

In some embodiments, provided herein are methods of treating cancer comprising: administering a composition to a subject, wherein the composition comprises nanoparticles encapsulating and/or conjugated to a drug, wherein the nanoparticles are neutral or nearly neutral in charge and less than 250 nm in diameter on average, wherein the subject has cancer cells in at least one bone, wherein the drug is an anti-cancer agent, and wherein the administering kills at least some of the cancer cells in the at least one bone.

In certain embodiments, provided herein are kits, systems, and compositions comprising: nanoparticles encapsulating and/or conjugated to a drug, wherein the nanoparticles are neutral or nearly neutral in charge and less than 250 nm in diameter on average, and wherein the drug is an anti-cancer agent.

In particular embodiments, the nanoparticles comprise poly (D,L-lactide-co-glycolide) (PLGA). In other embodiments, the nanoparticles comprise poly (D,L-lactide-co-glycolide) (PLGA) and a surface polymer. In certain embodiments, the surface polymer comprises poly (vinyl alcohol). In additional embodiments, the nanoparticles have a zeta potential between −5 and +5 mV (e.g., −5, −4, −3, −2, −1, 0, +1, +2, +3, +4, or +5 mV). In other embodiments, the nanoparticles have a zeta potential between −3 and +3 mV. In certain embodiments, the nanoparticles have an average diameter of about 100 to about 250 nm (e.g., 100 . . . 150 . . . 200 . . . or 250 nm).

In certain embodiments, the cancer cells are selected from the group consisting of: bone cancer cells, osteosarcoma cells, chondrosarcoma cells, Ewing's sarcoma cells, fibrosarcoma cells, prostate cancer cells, breast cancer cells, lung cancer cells, thyroid cancer cells, and kidney cancer cells. In further embodiments, the anti-cancer agent is selected from: an anticancer monoclonal antibody of binding fragment thereof; an anticancer small molecule; and a combination of the anticancer monoclonal antibody or the binding fragment thereof and the anticancer small molecule. In certain embodiments, the nanoparticles further encapsulate and/or are conjugated to, a RANKL (receptor activator of nuclear factor-kappa B ligand) inhibitor. In some embodiments, the RANKL inhibitor is selected from the group consisting of osteoprotegerin (OSG), an anti-RANKL antibody, or binding fragment thereof. In particular embodiments, the RANKL inhibitor comprises denosumab.

In some embodiments, provided herein are methods of treating a bone disease comprising: administering a composition to a subject (e.g., human subject), wherein the composition comprises nanoparticles encapsulating and/or conjugated to a RANKL inhibitor, wherein the nanoparticles are neutral or nearly neutral in charge and less than 250 nm in diameter on average, wherein the subject has a bone disease in at least one bone.

In particular embodiments, provides herein are kits, systems, and compositions comprising: nanoparticles encapsulating and/or conjugated to an RANKL inhibitor, wherein the nanoparticles are neutral or nearly neutral in charge and less than 250 nm in diameter on average.

In certain embodiments, the RANKL inhibitor is selected from the group consisting of osteoprotegerin (OSG), an anti-RANKL antibody, or binding fragment thereof. In other embodiments, the RANKL inhibitor comprise denosumab. In other embodiments, the bone disease is osteoporosis and/or osteopenia. In certain embodiments, rheumatoid arthritis is treated with the RANKL inhibitor with the NPs described herein.

DETAILED DESCRIPTION

Figure 1:
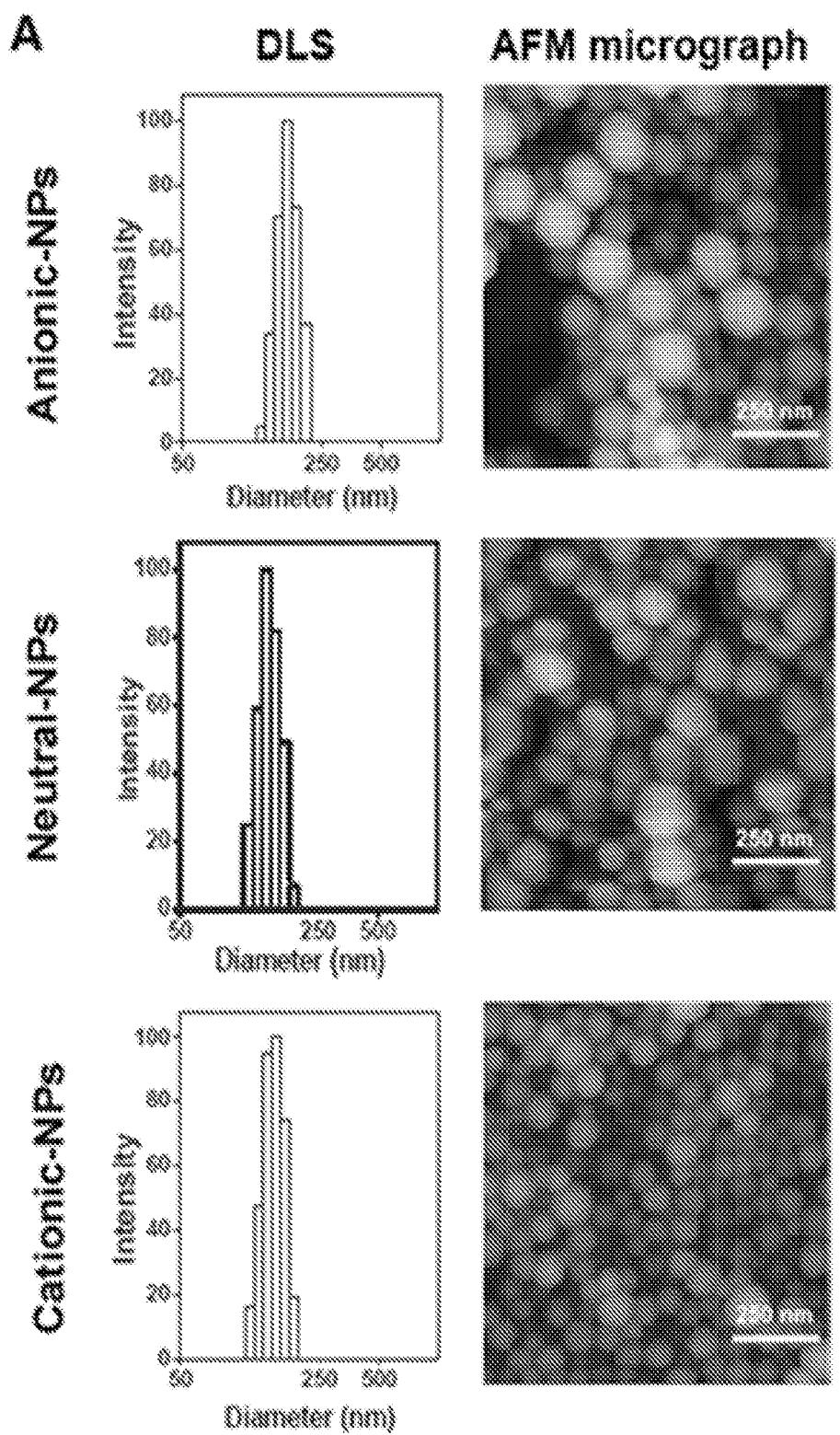
FIG. 1 shows results of physical characterization of different formulations of NPs. A) Characterization of anionic, neutral, and cationic NPs for particle size and size distribution by dynamic light scattering (DLS). NP size and shape characterization was determined by atomic force microscopy (AFM). B) Amount of surface-associated PVA with anionic, neutral, and cationic NPs. Data are shown as mean±s.e.m. n=3. C) Release of PTX in vitro from drug-loaded neutral NPs under sink conditions. Data are shown as mean±s.e.m., n=3.
Figure 1:
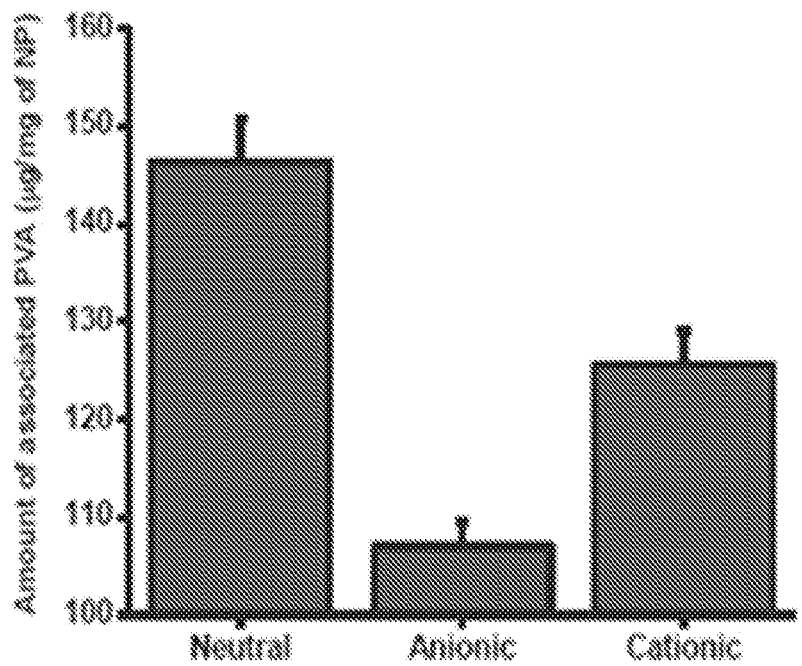
Figure 1:
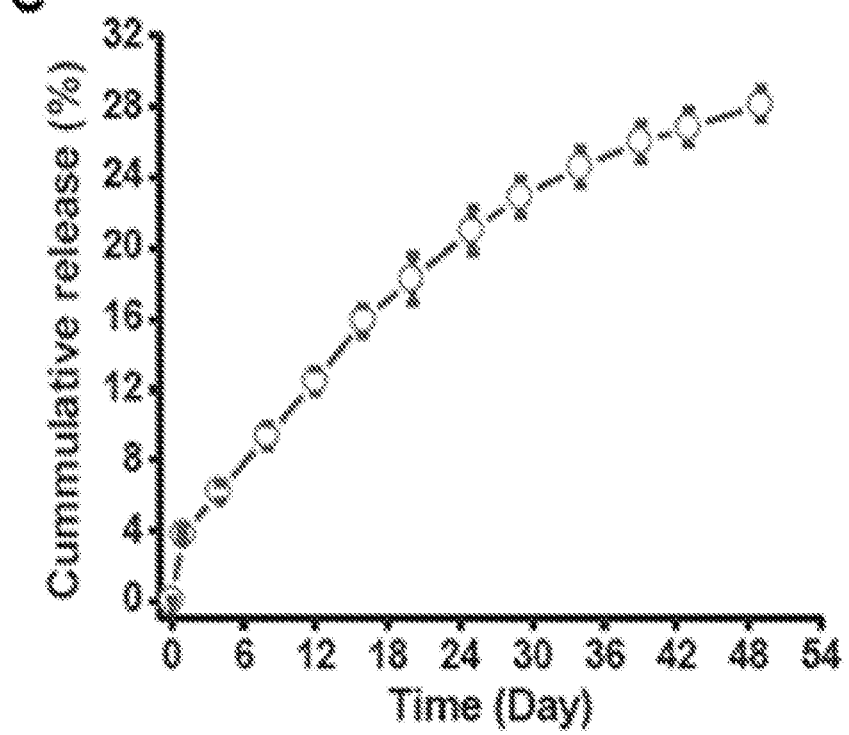

Provided herein are compositions, systems, kits, and methods for treating cancer in at least one bone of a subject using nanoparticles encapsulating, or conjugated to, an anti-cancer agent. In other embodiments, provided herein are composition, systems, kits, and methods for treating a bone disease (e.g., osteoporosis) in a subject using nanoparticle encapsulating, or conjugated to, a RANKL inhibitor. The nanoparticle are, in certain embodiments, neutral or nearly neutral in charge (e.g., zeta potential between −5 and +5 mV) and less than 250 nm in diameter on average (e.g. have an average diameter between 100 and 200 nm).

In certain embodiments, provided herein are biodegradable NPs that effectively localize to bone marrow to improve NP-mediated anticancer drug delivery to sites of bone metastasis to inhibit cancer progression and prevent bone loss. Word conducted during development of embodiments of the present disclosure demonstrated that: (a) following intravenous (IV) administration, NPs with a neutral surface charge were more effective in localization to and retention in marrow than anionic or cationic NPs and (b) a single dose of drug-loaded neutral NPs (e.g., PTX-NPs) inhibited progression of bone metastasis and prevented bone loss.

The present disclosure is not limited by the type of nanoparticles that are employed. The nanoparticles should be neutral or nearly neutral in charge (e.g., a zeta potential between −5 and +5 mV) and be less than 250 in average diameter (e.g., 100-200 nm's in average diameter). Nanoparticles may be composed of biodegradable polymers (e.g., as shown in Examples 1 and 2) or may be metallic nanoparticles. Nanoparticles can be metallic nanoparticles that are neutral and have an average diameter between, for example, 100 nm and 250 nm, including for example transition metal particles such as for example titanium, tantalum, niobium, iron, copper, ruthenium, molybdenum, nickel, cobalt, platinum, palladium, gold, or silver nanoparticles, or combinations of these metals or their alloys. In particular, conductive materials such as copper, gold, and silver can be used. In certain embodiments, the neural or nearly neutral nanoparticles are composed of Au, Pt, Pd, InAs, Si, InSb, InP, Ge, SiGe, oxide nanoparticles, and/or mixtures of these materials. The lipids used may be composed of triglycerides (e.g., tri-stearin), partial glycerides (Imwitor), fatty acids (stearic acid, palmitic acid), and steroids (e.g., cholesterol), waxes (e.g., cetyl palmitate) or combinations thereof. Nanoparticles could also be liposomes. Solid lipid NPs and liposomes consist of different lipids and surfactants such as Poloxamer 188, Soy phosphatidyl choline, Compritol, Cetyl palmitate, Tego care 450 or polymers, PEG 2000, PEG 4500, Tween 85, Ethyl oleat, Na alginate 70%, Ethanol/butanol, Tristearin glyceride, PEG 400, Isopropylmyristate, Pluronic F 68, Tween 80.

The nanoparticles can have a uniform structure. For example, the nanoparticle can contain one material or element in the particle. Nanoparticles can be solid or have a core shell structure. The nanoparticles can be lipid based nanoparticles. The nanoparticle can contain one material or element in the core and one material or element in the shell. The nanoparticles can be nanocrystals. The nanoparticles can be adapted to provide stability using for example stabilizers and surfactants. The nanoparticles can be magnetic nanoparticles.

In certain embodiments, the nanoparticles do not comprise poly-ethylene glycol (PEG), while in other embodiments, the nanoparticles do comprise PEG. In particular embodiments, the nanoparticles are formed from poly(lactide-co-glycolide) (PLGA). Methods of generating such PLGA nanoparticles are provide in Examples 1 and 2 below, and in Sah and Sah, "Recent Trends in Preparation of Poly(lactide-co-glycolide) Nanoparticles by Mixing Polymeric Organic Solution with Antisolvent," Journal of Nanomaterials, Volume 2015, pages 1-22, which is herein incorporated by reference in its entirety, including for the methods described therein for generating nanoparticles.

In certain embodiments, the drug (e.g., anti-cancer drug) or RANKL inhibitor is formulated as a solid lipid nanoparticle (see, e.g., U.S. Pat. No. 8,980,864, which is herein incorporated by reference). A solid lipid nanoparticle (SLN) may be spherical with an average diameter between 10 to 250 nm, or 100-200 nm. SLN possess a solid lipid core matrix that can solubilize lipophilic molecules and may be stabilized with surfactants and/or emulsifiers. In a further embodiment, the lipid nanoparticle may be a self-assembly lipid-polymer nanoparticle (see Zhang et al., ACS Nano, 2008, 2 (8), pp 1696-1702; herein incorporated by reference in its entirety). The art provides descriptions of how to make various types of nanoparticles that are neutral and less than 250 nm (e.g., see, The Book entitled "Nanoparticle Drug Delivery Systems," edited by Thassu, Deleers, and Pathak, 2007 by Informa Healthcare USA, ISSBN: 10: 0-8493-9073-7, which is herein incorporated by reference in its entirety, including for a description of how to make neutral nanoparticles containing or conjugated to a drug moiety that is less than 250 nm).

In certain embodiments, the NPs are formulated by a single oil-in-water emulsion solvent-evaporation method (e.g., with conditions generally optimized to obtain NPs of similar size and neutral or nearly neutral charge). For example, NPs with neutral or nearly neutral surface charge are formulated by modulating the amount of surface polymer (e.g., PVA) associated with NPs or using the cationic surfactant (e.g., CTAB) in combination with a surface polymer (e.g., PVA, as in previously described procedures [21, 22]). Surface polymer include, but are not limited to, ethylene oxide/propylene oxide diblock and triblock poly(ethylene glycol), pluronics and tetronics, acrylic acid and alkyl acrylate, fatty acids, sodium lauryl sulfate, and alpha olefin sulfonate. It is noted that the surface-associated emulsifier is that which remains associated with NPs at the interface despite repeated washing. The emulsifier remains because of the anchoring and integration of the hydrophobic segment of the emulsifier (polyvinyl acetate in the case of PVA or the acyl chain in the case of CTAB) with the polymer matrix at the interface. In certain studies, the role of the residual PVA on physical and biological properties (cellular uptake and intracellular trafficking) has been determined with respect to PLGA-NPs [23-26, all of which are herein incorporated by reference].

In particular embodiments, the nanoparticles are formed (e.g., primarily) from a biodegrable polymer, (D,L-lactide-co-glycolide) or another polymer such as: a caprolactone polymers, chitosan, hydroxybutyric Acids, Polyanhydrides, Polyesters, Polyphosphazenes, Polyphosphoesters, Lipodisq, or any combination thereof. In certain embodiments, the biodegradable polymer is selected from the group consisting of a poly(lactide-co-glycolide), poly(lactic acid), poly(alkylene glycol), polybutylcyanoacrylate, poly(methylmethacrylate-co-methacrylic acid), poly-alkylamine, polyanhydride, polyhydroxybutyric acid, a polyorthoester, or any combination thereof.

Figure 11:
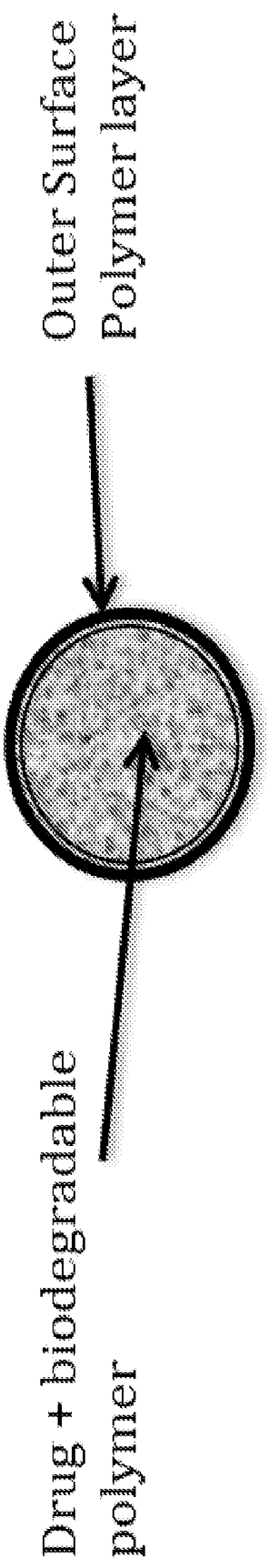
FIG. 11 shows a schematic of one embodiment of a nanoparticle, which shows a generally spherical shape with a core matrix made of biodegradable polymer with drug in it, and an outer Surface Polymer layer.

In certain embodiments, the nanoparticle are generally as shown in FIG. 11, which shows a generally spherical nanoparticle with a core matrix made of biodegradable polymer with drug in it, and an outer Surface Polymer layer. In such embodiments, the surface is modified with a surface polymer (e.g., PVA). To make anionic or neutral nanoparticles, one adjusts the amount of surface polymer associated with the surface of nanoparticles. At higher amount of surface polymer (e.g., PVA) nanoparticles generally become neutral whereas at lower amounts, they are generally anionic. To make them cationic, one can add a surface polymer and a cationic surfactant (e.g., CTAB, cethyl trimethylammonium bromide).

In certain embodiments, the polymer used to make the nanoparticles are biodegradable polymer (e.g., one which is brokendown in the body and are cleared) and are biocompatible. In certain embodiments, such polymer are hydrophobic. In some embodiments, the polymers are long-chain polymers that breakdown in the presence of water, releasing the content slowly. In particular embodiments, the polymers are linear or branched with hydrophobic and/or hydrophilic units. In some embodiments, the polymers are linear and/or branched or block co-polymers with combination of different polymer segments, functionalized or esterified.

In certain embodiments, the surface polymers have a hydrophobic chain and hydrophilic chain. In case of PVA, it is the combination of polyvinyl acetate which hydroponic and part of polyvinyl acetate is hydrolyzed to make polyvinyl alcohol which is hydrophilic. In some embodiments, the surface polymers have a balance of hydrophobic and hydrophilic segments so that they anchor onto the surface of the polymer at the interface (e.g., an acetate segment is buried into the matrix whereas alcohol segment is outside of the nanoparticles).

Advanced-stage prostate cancer often metastasizes to bone but becomes incurable due to poor biodistribution of intravenously administered anticancer drugs within bone. Bisphosphonates are currently used to reduce the risk of skeleton-related events and to ameliorate bone pain, but they do not improve survival. Injected drugs or drug-loaded nanocarriers conjugated to bone-seeking agents remain inefficient in treating bone metastasis. Provided herein (e.g., as a therapy for bone metastasis), in some embodiments, is a route for nanoparticle (NP)-mediated drug delivery to bone—the intracellular clefts between endothelial cells in bone marrow.

PEGylated NPs, because of their hydrophilic surface, remain in the circulation rather than efficiently extravasating through the fenestrations in bone-marrow capillaries. The approach provided herein provides non-PEGylated NPs with characteristics (size, charge, and surface composition) so that following their intravenous administration, these NPs do extravasate through the openings of the marrow's sinusoidal capillaries.

Work conducted during development of embodiments of the present disclosure, using a PC-3M-luc cell-induced osteolytic intraosseous mouse model of prostate cancer, (a) after intravenous injection, these NPs demonstrated focal accumulation in bone marrow within metastatic sites and (b) a single dose of drug-loaded NPs significantly inhibited the progression of bone metastasis and completely prevented bone loss.

In certain embodiments, the NPs described herein are employed to deliver a RANKL inhibitor to bone. In some embodiments, the RANKL inhibitor is denosumab (DNmb) is a monoclonal antibody that binds to receptor activator of nuclear factor-κB ligand (RANKL). Over expression of RANKL in the bone microenvironment drives the vicious destructive cycle of progression of bone metastasis and bone resorption. In certain embodiments, both anti-cancer and RANKL inhibitors are employed together. For example, DNmb is used as a targeting ligand against RANKL and docetaxel are combined with the NPs. Using the NPs herein, which effectively localize to bone, and the combination of DNmb and TXT with their complementary mechanism of action, are used to inhibit progression of bone metastasis and prevent bone loss (see FIG. 9).

Bone is a common site for metastasis in many human cancers, with devastating consequences, and bone metastasis is the major cause of morbidity and mortality in patients with prostate and breast cancers. The 5-year survival rate is much lower when cancer metastasizes to bone (~20% vs. 100% if localized). Because bone is less perfused than other organs (cardiac output 7% to bone vs. 30% to liver), intravenously administered chemotherapeutics cannot achieve therapeutic levels at bone metastatic sites. New approaches for drug delivery to bone are needed to effectively treat bone metastases. Despite their significance, nanocarriers for drug delivery to treat bone metastasis remains an under-researched area; most approaches focus on treating soft-tissue tumors. Bone marrow has sinusoidal capillaries with intercellular clefts as wide as 170 nm between endothelial cells; however, despite their long systemic circulation time and small size (smaller than the capillary fenestrations in bone marrow), PEGylated nanoparticles (NPs) cannot effectively extravasate into bone.

Work conducted during development of embodiments of the present disclosure show that (a) these NPs localize into sites of bone metastasis in a PC-3M-luc cell-induced osteolytic intraosseous model, and (b) a single-dose intravenous injection of drug (e.g., paclitaxel (PTX)) loaded NPs slowed progression of bone metastasis, prevented bone loss, and reduced acute drug toxicity. In contrast, an equivalent dose of PTX, delivered using a rapidly drug-releasing Cremophor EL formulation, aggravated tumor growth and caused weight loss.

In certain embodiments, the anti-cancer drug with the NPs is docetaxel (TXT). TXT is more potent than PTX and is the drug of choice to treat metastatic prostate cancers. In some embodiments, the combination of DNmb and TXT (or other combination of RANKL inhibitor and anti-cancer agent) is employed because of their complementary roles in preventing bone resorption and cancer progression. In particular embodiments, DNmb is employed as a targeting ligand for the NPs against RANKL in a metastatic bone micro-environment.

Figure 9:
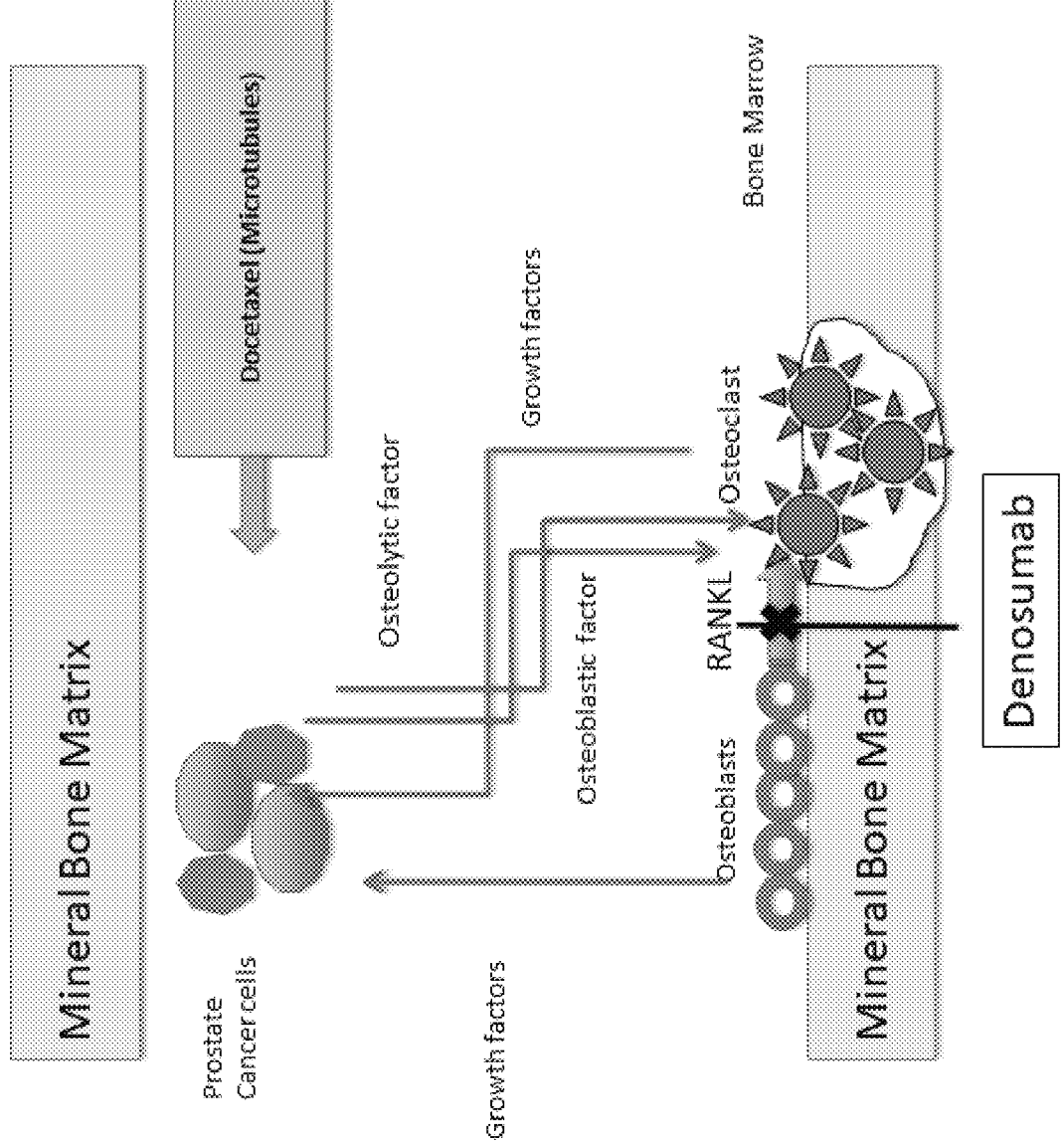
FIG. 9 shows a schematic of the action of RANKL inhibitor denosumab in the mineral bone matrix.

While the present invention is not limited to any particular mechanism, and an understanding of the mechanism is not necessary to practice the invention, it is believed that an RANKL inhibitor (e.g., Denosumab (DNmb)) delivered via the NPs herein, following intravenous injection, can form a depot in metastasized bone marrow, slowly releasing the encapsulated inhibitor (e.g., DNmb) within the tumor bone environment to control excess RANKL levels that can inhibit: a) the RANKL-RANK interaction to prevent osteoclast differentiation, function, survival, and hence bone resorption. Under normal circumstances, osteoprotegerin (OPG) produced by osteoblast binds to RANKL to maintain a balance but within the tumor bone environment, OPG production is downregulated by factors such as parathyroid hormone-related peptide, and other factors produced and secreted by tumor cells (IL-6, prostaglandin E2, TNF, and macrophage-colony stimulating factor), shifting the balance further towards greater RANKL availability which stimulates osteoclastogenesis; b) growth factors produced by differentiated osteoclasts that promotes cancer cell growth and proliferation to drive further progression of bone metastasis; c) the effect of RANKL produced by prostate cancer cells that promotes transformation of osteoblast to osteoclasts; and d) migration of circulating prostate cancer cells to bone marrow as RANKL is considered as chemo-attractant. Further, co-delivery of TXT (or similar agent), a microtubule inhibitor can induce cancer cell death in the marrow that can be synergistic with RANKL inhibitor-NPs (FIG. 9). Thus there are multiple pathways via which RANKL inhibitor-NPs (e.g., DNmb-nano) alone or in combination with anti-cancer-NPs (e.g., TXT-nano) can be effective in treating advanced stage cancer (e.g., prostate cancer) and minimizing skeletal related events that are common in bone metastasis.

Figure 10:
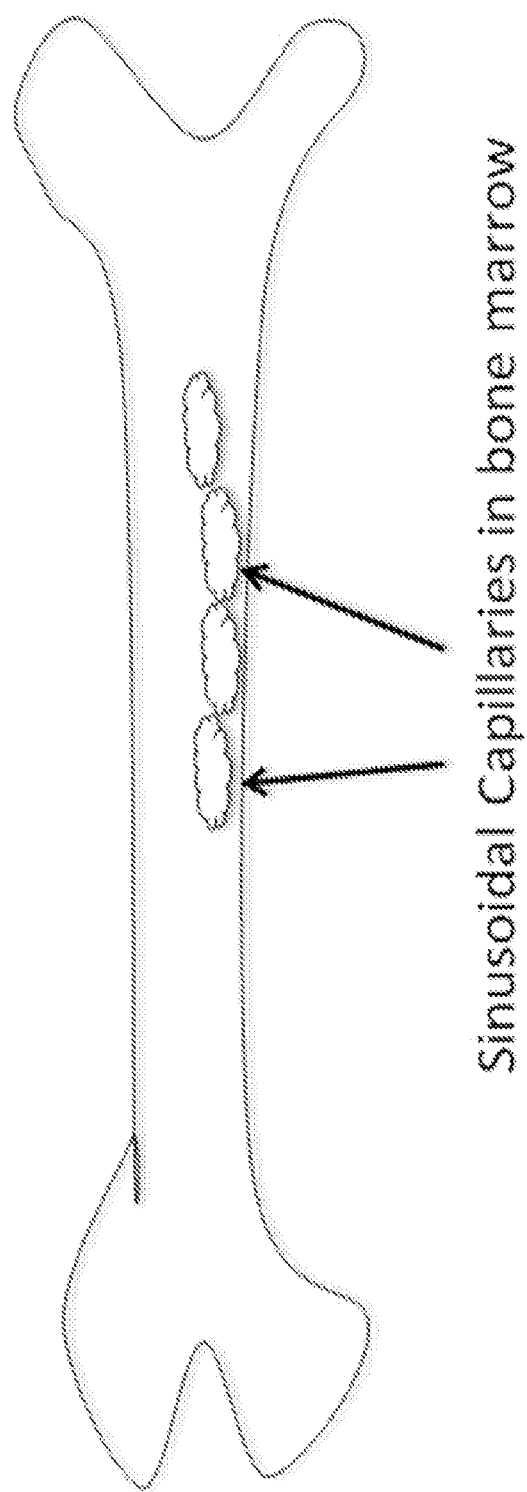
FIG. 10 shows a schematic showing sinusoidal capillaries in bone marrow.

Despite its significance, bone drug delivery using nanotechnology for treating bone metastasis remains an under-researched area.42 It is important to understand the bone marrow vasculature and the characteristics of NPs, both of which are important for the NPs' extravasation through bone marrow capillaries into the marrow itself. Bone marrow possesses sinusoidal capillaries with intracellular clefts between endothelial cells, and some of these clefts are as wide as 170 nm (FIG. 10) (and see refs. 43,44).

In certain embodiments, the NPs are constructed with some of all of the following characteristics: 1) small enough to pass through sinusoidal capillaries of bone marrow and be retained in the bone marrow; 2) large enough so that they do not pass through the sinusoidal capillaries of the liver or kidney; 3) remain in circulation for sufficient time to extravasate through sinusoidal capillaries of bone marrow; 4) reduce interactions with proteins to avoid clearance by the organs of the RES; and 5) non-pegylated to they may remain in circulation rather than extravasate through bone marrow capillaries. In certain embodiments, the NPs' surface is modulated to reduce the uptake of NPs by Kupffer cells to avoid hepatic uptake as well as minimize their interactions with complement-activating proteins to reduce clearance by the organs of the reticuloendothelial system (RES). Further, for therapeutic efficacy, sustained retention of the extravasated NPs in the bone marrow at the metastatic tumor site is also important.

Conventionally, NPs are modified with hydrophilic polymers such as polyethylene glycol (PEG; PEGylated NPs) or pluronics to sustain their time in the circulation. This is the approach commonly explored for delivery of anticancer therapeutics to vascularized primary tumors via the enhanced permeation and retention (EPR) effect.48 Modification of NPs with PEG/pluronics has been shown to improve biocompatibility of NPs, reduce particle aggregation, and PEG provides easy and flexible chemistry for conjugation to ligands for targeting.49 Further, PEGylated NPs have been shown useful in other applications (e.g., they diffuse more efficiently through the mucus barrier than non-PEGylated NPs).50,51 However, PEGylated/pluronic modified NPs are not effective in extravasating into the bone marrow.52 Several studies have reported that despite a long systemic circulation time and size smaller than the openings of the bone marrow capillary fenestrations, uptake of these NPs in the bone marrow remains insignificant.53 This could be due to their hydrophilic surface that keep them into circulation rather than extravasate through the bone marrow capillary fenestrations. Further, PEGylation causes reduced drug uptake by target cells due to hydrophilic surface of NPs,54 and also steric hindrance due to PEG diminishes ligand-receptor interactions by several hundred-folds as compared to the interactions when no PEG used for conjugation.55 These contrasting effects of PEG are commonly referred to as "PEGylation Dilemma"0.56 The PSMA-aptamer PEG conjugated NPs being developed by BIND Therapeutics, now in Phase II clinical trials for cancer treatment, are too large (~400 to 600 nm hydrodynamic diameter) to pass through the marrow's sinusoidal capillaries.32 NP albuminbound (nab) PTX (Abraxane®), despite having smaller particle size (~130 nm) than the openings of the bone marrow capillary fenestrations (~170 nm) has in fact been shown to increase the incidence of metastasis, including to bones, in an animal model of breast cancer metastasis.57 This effect could be due to its rapid drug releasing profile (<1 hr), thus not being able to deliver and maintain a therapeutic dose of the drug directly at the bone metastatic site (see more discussion about this point under Research Strategy below).

In work conducted during the development of embodiments of the present invention, NPs with an anionic, neutral or cationic surface charge were formulated by modulating the amount of PVA associated with NPs or using the cationic surfactant cetyltrimethylammonium bromide (CTAB) in combination with PVA as per the previously described procedures.64,65 It is important to note that the surface-associated emulsifier remains associated with the NP surface, despite repeated washing of NPs. This condition occurs because of the anchoring and integration of the hydrophobic segment of the emulsifier (polyvinyl acetate in the case of PVA or an acyl chain in the case of CTAB) with the polymer matrix at the interface. In several studies, it has been determined that the role of the residual PVA on physical and biological properties of (cellular uptake and intracellular trafficking) of PLGA-NPs.66-69 Similarly, it was shown that the combination of PVA and a cationic surfactant, when used as an emulsifier, can impart a cationic charge to PLGA-NPs.70 Importantly, a significant fraction of PVA remains associated with NPs over several days when incubated in PBS at 37° C.71 This means that the NPs' surface composition would be maintained for a period of time following their intravenous injection. In work conducted herein, the high-pressure homogenization conditions (EmulsiFlex C5; Avestin, 10 cycles at 10,000 psi) were optimized to obtain NPs in the desired size range. In certain embodiments, various additives (e.g., plasticizers and pore-forming agents) are employed to modulate the release of drugs (e.g., hydrophobic drugs, such as U-86983) from the NPs described herein. In certain studies, it was found that L-tartaric acid dimethyl ester (DMTA), a low-molecular-weight compound (MW=178) made from naturally occurring L-tartaric acid, is effective in modulating the drug-release rate.98 DMTA is inert and soluble in both organic and water solvents, is compatible with PLGA, and is effective in creating pores, thus acting as a plasticizer. In certain studies, it was found that the rate of drug release from matrix depends on the percent of DMTA (5%-20% w/w) added into the polymer mass. At 10% DMTA, the drug release rate was ~5 times the rate without it. Therefore, in some embodiments, the NPs comprises 3-35% DMTA, or similar agent, to modulate the release of drugs form the NPs. For example, this approach may be used to modulate the TXT-release rate from PLGA-NPs. For formulating NPs, DMTA (5%-20% w/w polymer mass) and PLGA or other biodegradable polymer along with TXT is dissolved in the organic solvent prior to emulsification.

In certain embodiments, NPs with RANKL inhibitors are employed. For example, DNmb-NPs are formulated using PLGA (or other biodegradable polymer) with DMTA (or other poreforming agent) added. Because of its poreforming ability, DMTA incorporated into PLGA polymer (1:9 w/w) allows free diffusion of the acidic oligomers (polylactic and polyglycolic acids) that form as a result of polymer degradation. These acidic oligomers, if trapped within NPs, are known to denature encapsulated enzymes/proteins, influencing their biological activity and incomplete release.99 It has been previously shown that sustained release enzymes (superoxide dismutase, SOD and catalase, CAT) in active form with 8.2±1.6% cumulative release in 24 h, 26.8±1.5% in 1 wk, 41.5±3.2% in 4 wk, and 78±9.3% in ~3 mo.100 It has also been shown that this formulation composition is effective for sustained release of other proteins (vascular endothelial growth factor; basic fibroblast growth factor) in active form, with 12% cumulative release in 24 hrs, 60% release in 5 wks and 100% in 9 wks.101 Similar approaches are used to formulate DNmb-nano (DNmb Mol wt 147KD whereas that of SOD is 32.5 KD and that of CAT is 68.9 KD) and modulate the release rate using different ratio of polymer to DMTA as described above.

In certain embodiments, the NPs described herein contain or are conjugated to an anti-cancer agent. Table 5 provides a list of exemplary anti-cancer agents that may be employed with the nanoparticles described herein.

TABLE 5

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N'',-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus* Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chloroethyl)amino]benzenebutanoic acid) | Leukeran | Glaxo SmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Done | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |

TABLE 5-continued

| | | |
|---|---|---|
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$•$(C_2H_4O_2)_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |

TABLE 5-continued

| | | |
|---|---|---|
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperidinopiperidino)carbonyloxy]-1H-pyrano[3',4':6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl1,4,5,6,7,8 hexahydro4oxo-6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \bullet HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6 H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5ß,20-Epoxy-1,2a,4,7ß,10ß,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |

TABLE 5-continued

| | | |
|---|---|---|
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethyletnanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumornab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R—(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

EXAMPLES

The following examples are illustrative and not intended to limit the scope of the present invention.

Example 1

Inhibition of Bone Loss with Surface-Modulated, Drug-Loaded Nanoparticles in an Intraosseous Model of Prostate Cancer In this example, the surface charge/composition of biodegradable nanoparticles (NPs) was modulated to sustain their blood circulation time and they were made small enough to extravasate through the openings of the bone's sinusoidal capillaries and thus localize into marrow. NPs with a neutral surface charge, achieved by modulating the NP surface-associated emulsifier composition, were more effective at localizing to bone marrow than NPs with a cationic or anionic surface charge. These small neutral NPs (~150 nm vs. the more usual ~320 nm) were also ~7-fold more effective in localizing in bone marrow than large NPs.

Such NPs localize to bone marrow thereby improve NP-mediated anticancer drug delivery to sites of bone metastasis, thereby inhibiting cancer progression and preventing bone loss. In a PC-3M-luc cell-induced osteolytic intraosseous model of prostate cancer, these small neutral NPs demonstrated greater accumulation in bone within metastatic sites than in normal contralateral bone as well as colocalization with the tumor mass in marrow. Significantly, a single-dose intravenous administration of these small neutral NPs loaded with paclitaxel (PTX-NPs), but not anionic PTX-NPs, slowed the progression of bone metastasis. In addition, neutral PTX-NPs prevented bone loss, whereas animals treated with the rapid-release drug formulation Cremophor EL (PTXCrEL) or saline (control) showed >50% bone loss. Neutral PTX-NPs did not cause acute toxicity, whereas animals treated with PTX-CrEL experienced weight loss.

Materials and Methods

Materials included the following: Poly (D,L-lactide-co-glycolide) (PLGA; 50:50, inherent viscosity of 0.26-0.54 dL/g) was purchased from LACTEL Absorbable Polymers (Birmingham, Ala.). Poly (vinyl alcohol) (PVA; 87-90% hydrolyzed, mol wt 30,000-70,000), sucrose, Cremophor EL (CrEL) and cetyltrimethylammonium bromide (CTAB) were purchased from Sigma-Aldrich (St. Louis, Mo.). Near-infrared (NIR) dye (SDB5700) was obtained from H.W. Sands Corp. (Jupiter, Fla.). Chloroform was obtained from Fisher Scientific (Pittsburgh, Pa.). Paclitaxel (PTX) was purchased from LC Laboratories (Woburn, Mass.).

Formulation and Characterization of NPs of Different Surface Charges.

NPs were formulated by a single oil-in-water emulsion solvent-evaporation method, but conditions were optimized to obtain NPs of similar size but different surface charges. Briefly, NPs with either an anionic, neutral or cationic surface charge were formulated by modulating the amount of PVA associated with NPs or using the cationic surfactant CTAB in combination with PVA, as per our previously described procedures [21, 22] (see Supplemental Material). It is important to note that the surface-associated emulsifier is that which remains associated with NPs at the interface despite repeated washing. The emulsifier remains because of the anchoring and integration of the hydrophobic segment of the emulsifier (polyvinyl acetate in the case of PVA or the acyl chain in the case of CTAB) with the polymer matrix at the interface. In several of previous studies, the role of the residual PVA on physical and biological properties (cellular uptake and intracellular trafficking) was determine for PLGA-NPs [23-26, all of which are herein incorporated by reference, particularly for nanoparticle generation]. To study the effect of size, PLGA NPs of larger size than those used above were also formulated and tested for their localization in bone (see further below). To monitor their biodistribution in vivo, NPs were loaded with NIR dye SDB5700. This dye has previously been evaluated for in vivo imaging and biodistribution of NPs in breast [27] and prostate [22] xenograft models. The dye offers several advantages, including a stable signal (even after repeated laser exposure), a high-fluorescence yield, no background signal, and only an insignificant amount of dye leaching from NPs because of the hydrophobic nature of the dye and its low loading (0.1% w/w polymer weight) [22].

PTX-loaded NPs were formulated to determine therapeutic efficacy. The hydrodynamic diameter and ζ-potential of NPs were determined in water by dynamic light scattering with a NICOMP 380 ZLS (Particle Sizing Systems, Santa Barbara, Calif.). In addition, NPs were characterized for surface-associated PVA, surface morphology, and size using atomic force microscopy (AFM) [22]. PTX loading in NPs was determined by extracting the drug from NPs using methanol. PTX release from NPs was carried out in double diffusion chambers under sink conditions as described previously [28]. PTX levels in samples were analyzed by high-performance liquid chromatography (see further below for detailed methods used for formulation and characterization of NPs).

Animal Studies.

Cleveland Clinic's Institutional Animal Care and Use Committee approved all animal procedures, and these were carried out according to federal and internal guidelines. Studies were performed with 5- to 6-week-old male athymic nude mice (Charles River Laboratories, Wilmington, Mass.).

Biodistribution of NPs.

A single dose of a 100-μL suspension of NIR dye-loaded NPs (30 mg/mL) in saline was injected via tail vein into each mouse, and animals were imaged at different time points post injection with a Maestro EX Imaging system (PerkinElmer, Waltham, Mass.) using blue and NIR filters set at exposure times of 500 ms and 1200 ms, respectively. To visualize localization and relative quantification of signal intensity (in counts) due to NPs in bone, the skin, muscles, and fat were removed to expose skeletons prior to imaging as above. To quantify relative signal intensity due to NPs localized in tibia, the region of interest (ROI) covering the entire tibia was used. Although other bones were analyzed for NP localization, this example focuses on the tibia because this is the most common site used for tumor induction, as described below.

Induction of Bone Metastasis and Imaging.

PC-3M-luc cells (obtained from the NIH) were cultured in RPMI 1640 supplemented with 10% FBS at 37° C. and 5% $CO_2$. Bone metastasis was induced as described by Park et al. [29]. Briefly, mice under ketamine/xylazine anesthesia were injected with 4×105 PC-3M-luc cells in 20 μL PBS intraosseously in the lumen of the right tibia, then monitored for induction of bone metastasis and its progression using changes in bioluminescence signal intensity (photons per second per square centimeter steradian; [p/sec/cm2/sr]) and micro-computed tomography (micro-CT) to determine bone loss. For bioluminescence, animals were imaged 15 min following intraperitoneal injection of luciferin (200 mg/kg; VivoGlo™ Luciferin, Promega, Madison, Wis.) using the IVIS® Lumina II (PerkinElmer). In addition, the IVIS® Lumina II was used to co-register the bioluminescence signal of cancer cells and the fluorescence signal of the dye-loaded NPs in metastasized bone. To determine bone loss, limbs resected at the head of the femur were imaged using an in vivo micro-CT for preclinical procedures (eXplore Locus RS Micro-CT, GE Healthcare, London, ON, Canada). The micro-CT images were acquired using an X-ray tube (80 kV, 490 μA) for an exposure time of 1.8 seconds. The detector bin was set to 1×1 spatial resolution, providing a full resolution of 20 Images were acquired for every degree of rotation, creating 360 raw data projections. These projections were corrected, unwrapped and reconstructed using GE's proprietary reconstruction algorithms to create a full three-dimensional reconstruction of the scanned specimen.

Flow cytometry analysis of bone marrow cells. To determine cellular uptake of NPs in bone marrow, animals without tumor were injected with NIR dye-loaded NPs (3 mg in 100 μL saline) and euthanized 24 hours following injection. Their femurs were resected and flushed with saline to recover the bone marrow. The collected marrow was incubated in red blood cell lysis buffer (Sigma-Aldrich) for 10 min, centrifuged to recover nucleated cells, and washed twice with saline. Flow cytometry was performed on nucleated cells in the red channel to determine the percentage of cells with dye-loaded NPs (BD FACSAria II, BD Biosciences, San Jose, Calif.).

Treatment to Determine Efficacy of PTX-Loaded NPs.

Micro-CT and bioluminescence signals confirmed the induction of tumor in marrow at 7 days post inoculation. At this point, mice with confirmed intraosseous metastases were divided into three groups, receiving: (a) a single-dose IV injection of PTX in Cremophor/ethanol (PTX-CrEL), (b) PTX-NPs (dose of PTX=7 mg/kg or 110 mg/kg PTX-NPs), or (c) saline as a control. The PTX dose was calculated from the standard dose of 175 mg/m2 used in prostate cancer patients. Tumor growth was monitored by weekly bioluminescence imaging of cancer cells using IVIS®. At 5 weeks post treatment, animals were euthanized, and both hind legs were harvested. The difference in the weight of the contralateral leg and the tumor-bearing leg was used to calculate tumor burden [30, 31].

Formulation of NPs of Different Surface Charges and Size

In a typical procedure, 90 mg PLGA was dissolved in 3 mL chloroform; this was then added to 12 mL of either 1% w/v PVA solution to form anionic NPs or 2% w/v PVA to form neutral NPs. To prepare cationic NPs, a polymer solution was emulsified into a 1% PVA solution containing 4 mM cetyltrimethylammonium bromide (CTAB). The polymer and PVA solutions were vortexed for 30 sec, and then sonicated using a probe sonicator (XL 2015 Sonicator Ultrasonic processor, Misonix, Inc., Farmingdale, N.Y.) for 3 minutes in an ice bath. The resulting emulsion was passed through a high-pressure homogenizer (EmulsiFlex C5; Avestin, Ottawa, ON, Canada) for 10 cycles between 5,000-10,000 psi to reduce particle size. For cationic NPs, the emulsion was sonicated for 5 minutes as above, but without homogenization. The emulsions were stirred overnight in a fume hood and the formed NPs were recovered by ultracentrifugation at 30,000 rpm (Rotor 50.2Ti, Beckman L80, Beckman Coulter, Inc., Brea, Calif.) at 4° C. for 30 min. NPs were washed twice with water, resuspended in 3% sucrose solution in water prior to lyophilization for 2 days at −48° C., 3.5 Pa (FreeZone 4.5, Labconco Corp., Kansas City, Mo.). To prepare dye-loaded NPs, 100 μg SDB5700 was added to the polymer solution to formulate anionic and neutral NPs; 200 μg SDB5700 was used to formulate cationic NPs. The amount of dye required for formulating cationic NPs was higher than that used for anionic or neutral NPs because a fraction of the added dye in the polymer solution partitioned into the CTAB micelles formed in the external aqueous phase. The dye amounts used for different formulations were optimized such that the signal intensity of all NPs was very similar. Large-sized NPs were formulated using identical protocol to that used for making anionic NPs but without the homogenization step. To formulate PTX-loaded neutral NPs, 6 mg PTX was added to the polymer solution and processed as above.

Characterization of NPs of Different Surface Charge

The mean hydrodynamic diameter of nanoparticles (NPs) was determined by dynamic light scattering with a Nicomp 380 ZLS (Particle Sizing Systems, Santa Barbara, Calif.). A 100 m/mL suspension of NPs in water was sonicated on ice for 30 seconds, and a 50 μL aliquot was added to a borosilicate glass disposable culture tube (Kimble Chase, Vineland, N.J.) for particle sizing. The same NP suspensions were used to measure the zeta potential in the dual-phase analysis and current mode at a scattering angle of −14°. Surface morphology of NPs was determined by atomic force microscopy on air-dried NPs coated onto silicon wafers. Before use, the silicon wafers (Ted Pella, Inc., Redding, Calif.) were cleaned by immersion into a mixture of H2O/H2O2/NH4OH (4:1:1 volume) at 80° C. for 5 minutes, rinsed with ultrapure water and dried under continuous N2 flow. A 100-μL aliquot of freshly prepared NPs suspension in water was applied onto the cleaned silicon wafer inclined at an angle of 25° to ensure uniform spread of the NPs and dried in a dust-free environment. A BioScope II Atomic Force Microscope (Bruker Nano Surfaces, Santa Barbara, Calif.) using a 125-μm-long silicon probe with resonance frequency of ~300 Hz and a tip radius <10 nm (Ted Pella, Inc., Redding) was used for imaging in tapping mode at a scan speed of 0.5 Hz and a set-point ratio of 1.0 at a resolution of 512×512 pixels. Images were flattened using a second-order flattening routine in Nanoscope software version 7.30 (Bruker Nano Surfaces, Santa Barbara, Calif.).

Estimation of Amount of PVA Associated with NPs

To determine the amount of polyvinyl alcohol (PVA) associated with NPs, to 1 mL suspension of each NPs (1 mg/mL) in water, 2 mL of 0.5 M NaOH was added and incubated at 60° C. for 15 minutes. Following incubation, 900 μL of 1 M HCl was added to each suspension and diluted with 1.1 mL water. To the above suspension, 3 mL boric acid was added followed by 0.5 mL I2/KI (0.05 M/0.15 M) and the total volume of the reaction mixture was made up to 10 mL by adding 1.5 mL water. The reaction was continued at room temperature for 15 minutes. Absorbance of the Iodine-PVA complex formed was measured at 690 nm using a spectrophotometer (DU 640B, Beckman Coulter, Brea, Calif.). A standard plot for PVA was prepared in the concentration range of 0-1000 m/mL PVA in water. Neutral-NPs show 38% and 18% more residual PVA than anionic and cationic NPs, respectively.

Drug Loading and Drug Release from PTX-NPs

PTX loading in NPs was determined by extracting PTX from NPs by incubating 2 mg NPs in acetonitrile for 48 hours at 4° C. Drug release from NPs was carried out in double diffusion chambers separated by a 0.1 μm membrane filter (Millipore, Billerica, Mass.). Sink condition was achieved using 0.1% (v/v) Tween-80 (Sigma, St. Louis, Mo.) in phosphate-buffered saline (PBS) containing 0.1% sodium azide as a preservative. The donor chamber of each diffusion chamber was filled with 2 mL buffer containing 2 mg NPs; the receiver chambers contained 2 mL release buffer without NPs. Filled diffusion chambers were rotated on an orbital shaker at 100 rpm at 37° C. The entire content of receiver chambers was collected at different time points and replaced with fresh release buffer. Collected samples were frozen at −80° C. and lyophilized; PTX from each sample was extracted with 300 μL acetonitrile. The amount of PTX in each sample was determined by high-performance liquid chromatography (Shimadzu Scientific Instruments, Columbia, Md.) with a Kinetex C-18 column (Phenomenex, Torrance, Calif.) using acetonitrile/water (50:50) as the mobile phase; injection volume was 25 μL. PTX was detected with an ultraviolet detector at 228 nm at an elution time of 5.1 minutes. A standard plot was constructed for PTX in the concentration range of 0-1000 μg/mL. PTX extracted from NPs to determine drug loading was analyzed using the above method.

Evaluation of Accumulation of Large-Sized and Neutral NPs into Bones

Mice were sacrificed 24 hrs post tail vein injection with 100 μL suspension of NIR dye-loaded NPs (30 mg/mL) in saline. The skin, muscles, and fat were carefully removed to expose the skeleton, which was imaged with Maestro Ex Imaging system (PerkinElmer, Waltham, Mass.) using blue and NIR filters set at exposure time of 500 ms and 1200 ms, respectively. Region of interest was drawn around the whole skeleton to quantify the relative amount of NPs localized within bones.

Efficacy of PTX-Loaded Anionic NPs

Intraosseous tumors were induced by injecting 4×105 PC-3M-luc cells in 20 μL PBS into the lumen of the right tibia. After confirmation of intraosseous tumor at 7 days post inoculation, mice were divided into different treatment groups and received either a single-dose intravenous injection of PTX-loaded anionic NPs (dose of PTX=7 mg/kg or 110 mg/kg PTX-NPs) or saline. Progression of tumor was followed for 3 weeks after treatment by bioluminescence imaging using IVIS® Lumina II.

Statistical Analysis.

All numerical data were expressed as mean±standard error of the mean. Statistical significance for both NP uptake by bone marrow cells and their localization in metastatic sites was determined by Student's t test. One-way analysis of variance was performed to analyze the biodistribution and localization of different NP formulations in tibia and also for therapeutic efficacy studies. Statistical significance was set at $P<0.05$ Results NP Formulation and Characterization.

All small NP formulations showed a similar hydrodynamic diameter and size distribution (polydispersity index) but varied in their surface charge (ζ-potential) (Table 1, FIG. 1). AFM images of the NPs showed their spherical shape, irrespective of surface charge (FIG. 1A). Mean NP diameter as determined by AFM was smaller than the hydrodynamic diameter measured in water using the dynamic light scattering technique (Table 1). The larger NPs had a mean hydrodynamic diameter of 321 nm (range, 248-460 nm; polydispersity index, 0.1) and ζ-potential of −15 mV. As determined, surface-associated PVA was greater for neutral NPs (146 µg/mg NPs) than for cationic (125 µg/mg NP) or anionic (106 µg/mg NP) NPs (FIG. 1B). There was no significant difference in size and ζ-potential of the dyeor drug-loaded NPs compared with the respective NPs formulated without dye or drug (Table 1). PTX loading in NPs was 6.4±0.3% w/w and demonstrated 28% cumulative drug release over 7 weeks (FIG. 1C). Also, since only an insignificant amount of the incorporated dye leaches out from NPs (5% over 4 days under sink conditions), due to the hydrophobic nature of the dye, its high solid-state solubility (no phase separation) in PLGA polymer [32], and very low dye loading in NPs (~0.1% w/w), we considered that the signal seen is primarily from the NPs themselves and not from the released dye. All three small NP formulations with different surface charges had similar signal intensity per unit weight of NPs (~14 counts per microgram of NPs), which allowed us to compare their relative biodistribution (including in marrow) based on optical signal intensity measured using Maestro. Signal intensity of large NPs was 13 counts per microgram of NPs.

TABLE 1

Characteristics of different formulations of nanoparticles

| NP Formulations | Diameter by DLS (nm)/PI* (Range) | Diameter by AFM (nm)** (Range) | ζ-Potential (mV)* |
|---|---|---|---|
| Anionic NPs (without dye) | 164 ± 5/0.055 (139-189 nm) | 112 ± 5 (65-175 nm) | −18 ± 2 |
| Dye-loaded anionic NPs | 168 ± 3/0.035 (159-177 nm) | ND | −17 ± 2 |
| Neutral NPs (without dye) | 152 ± 4/0.020 (136-168 nm) | 112 ± 4 (73-178 nm) | −2 ± 3 |
| Dye-loaded neutral NPs | 148 ± 2/0.022 (144-152 nm) | ND | −3 ± 3 |
| Cationic NPs (without dye) | 162 ± 23/0.088 (139-185 nm) | 91 ± 4 (44-136 nm) | 13 ± 1 |
| Dye-loaded cationic NPs | 169 ± 8/0.063 (161-177 nm) | ND | 12 ± 1 |
| PTX-loaded NPs | 151 ± 6/0.028 (145-157 nm) | ND | −2 ± 3 |

*Data are shown as mean ± standard deviation; n = 3.
**Diameter by AFM was measured using section profile analysis of 40 individual NPs.
ND. Not determined; nm. nanometer.

Biodistribution of NPs with Different Surface Charges.

Figure 2:
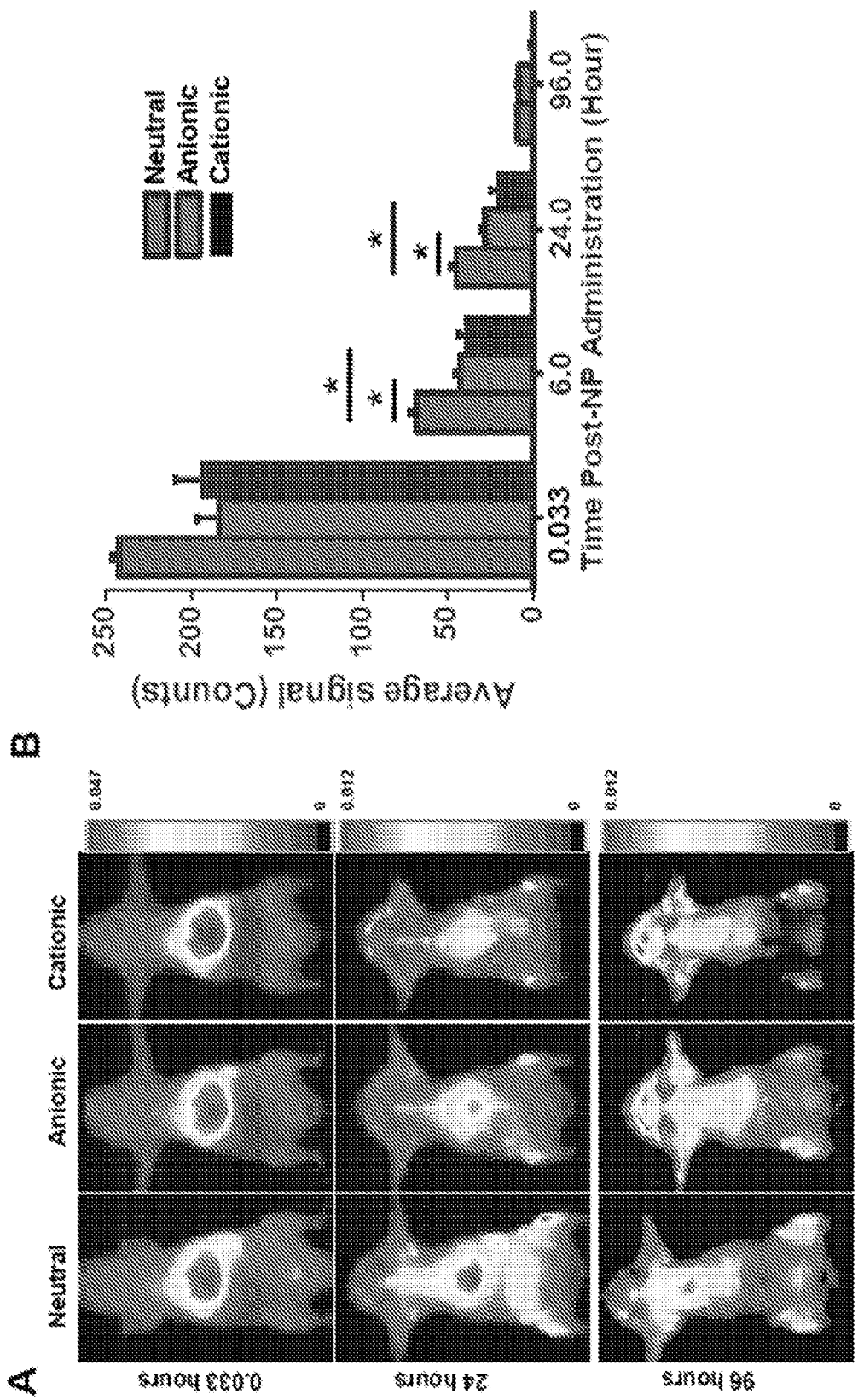
FIG. 2 shows the biodistribution of NPs with different surface charges. A) Whole-body images taken over time indicated prolonged retention of neutral NPs in the body. B) Quantification of the region of interest (ROIs) of the skin over time as measured using Maestro, demonstrating more prolonged body retention of neutral NPs than of anionic or cationic NPs. Data are shown as mean±s.e.m., *P<0.05; n=3.
Figure 6:
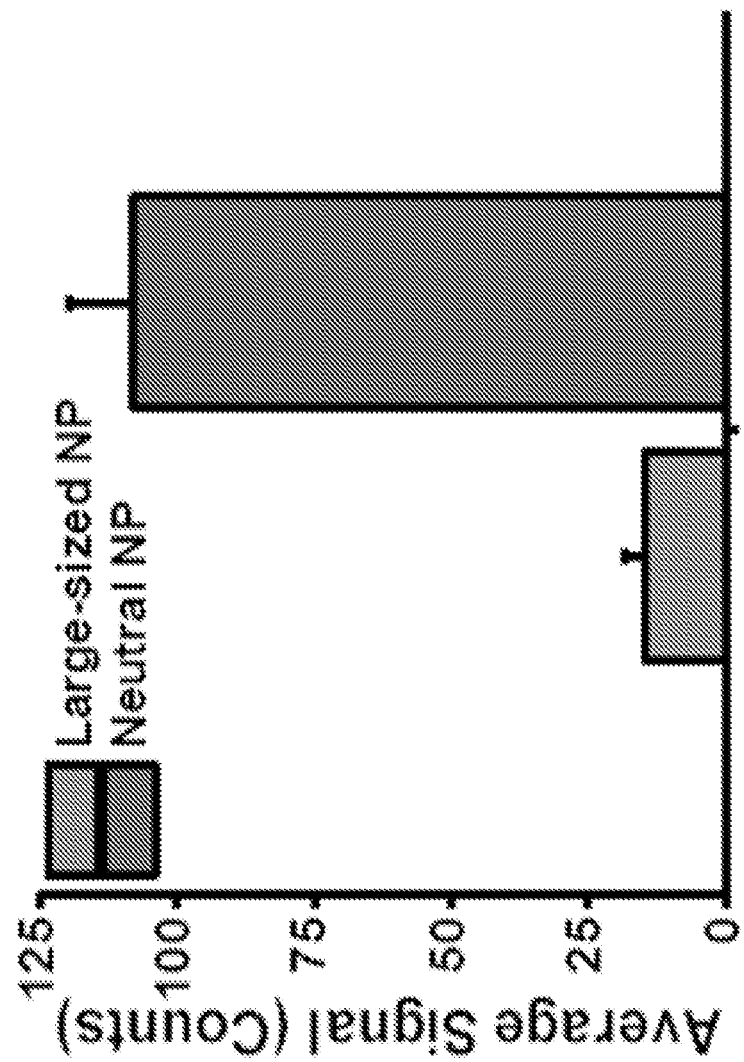
FIG. 6 shows the relative accumulation of large-sized NPs in comparison to neutral NPs in skeletons. Neutral NPs shows 7-fold greater accumulation into bones than large-sized NPs. Data are shown as mean±s.e.m., P<0.05; n=3.

The initial biodistribution study was carried out in normal mice (without tumor) to determine which formulation of NPs would show better localization and retention in bone marrow. The imaging data showed differences in the biodistribution of NPs, particularly over time, as a function of their charge. Immediately following injection (2 min), all formulations of NPs primarily showed localization in the liver; however, this biodistribution changed as time went on (FIG. 2A). Quantification of regions of interest (ROIs) for "skin" at the lower left abdominal area, which we considered as the signal attributable to the NPs in the circulation, demonstrated that neutral NPs remain in the circulation longer than anionic and cationic NPs do (FIG. 2B). This method of tracing skin signals to determine the relative circulation time of NPs has been used previously [21, 33]. While direct measurement of NPs in blood is required for absolute quantification of NPs, the method of skin tracing enables longitudinal monitoring of NPs in the circulation over time and correlates with direct blood measurements. Quantification of the ROIs of the tibia at 24 hours post NP administration showed 52% and 41% greater accumulation of neutral NPs than cationic or anionic NPs, respectively. At 96 hrs post injection, the accumulation of neutral NPs in tibia was 2.5-fold higher than anionic or cationic NPs (FIG. 3A). In a separate set of experiments, animals were euthanized and dissected at 24 hrs post injection of neutral NPs to visualize their biodistribution in other bones. Besides localization in the tibia and sternum, neutral NPs were seen in all the bones. Based on signal intensity, a greater accumulation of neutral NPs was seen in the pelvis and vertebral column than in the ribs and craniofacial bones (FIG. 3B). In the vertebral column, neutral NPs were seen more in thoracic than in lumbar vertebrae (FIG. 3C). A close-up image of the tibia showed localization of neutral NPs in the marrow rather than in the bone tissue (FIG. 3D), which was further confirmed from flow cytometry analysis of the marrow, which showed 90% of the nucleated cells with NPs (FIG. 3E, F). As seen in the tibia, an excised section of the femur also showed localization of NPs in the marrow (image not shown). The whole-body skeleton imaging showed an approximately 7-fold greater accumulation of small neutral NPs in bones than large NPs (FIG. 6).

Nanoparticle Localization in Metastasized Bone.

Figure 4:
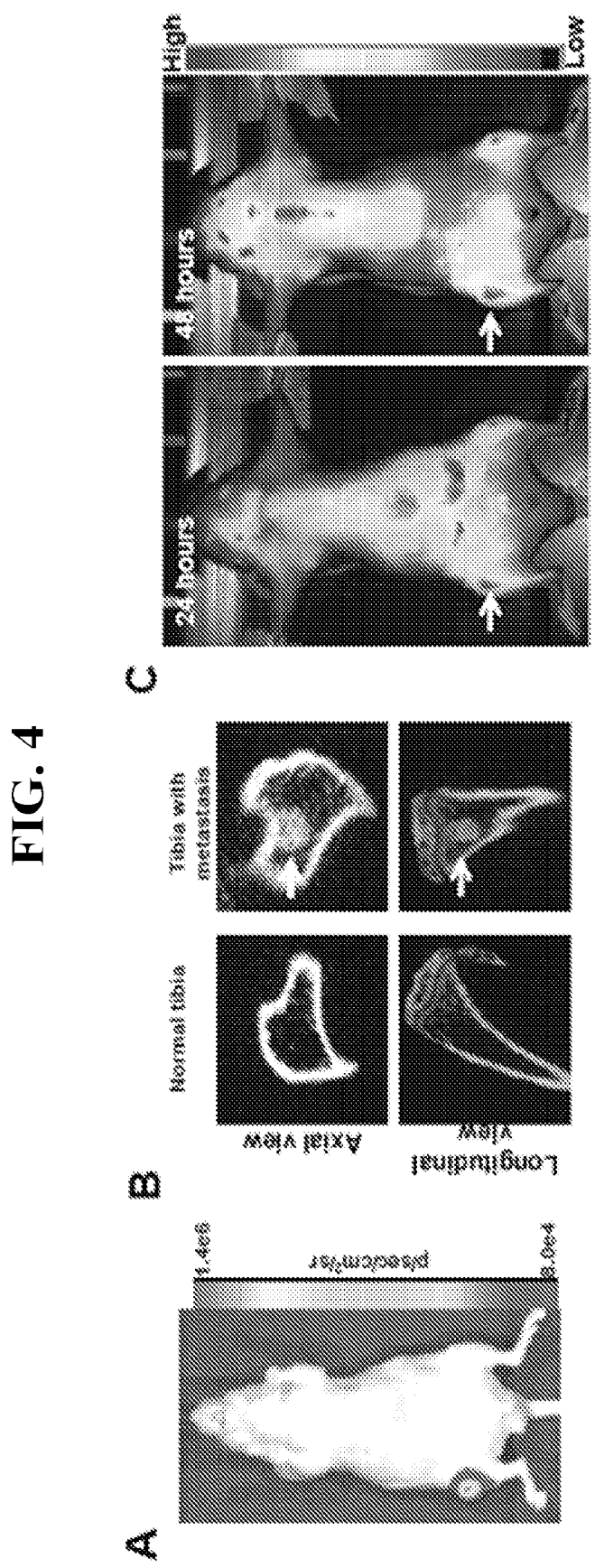
FIG. 4 shows localization of neutral NPs at site of tumor metastasis in bone. A) Bioluminescence signal due to PC-3M-luc prostate cancer cells at 7 days post inoculation as measured using IVIS® and B) micro-CT images of the bone at 7 days post cancer cell inoculation. C) Fluorescence imaging and D) quantification of signal intensity measured using Maestro, demonstrating greater localization of NPs in tibia with tumor than in normal contralateral tibia. E) Ex vivo image (by Maestro) of the bone with intraosseous tumor at 24 hrs following NP administration. Arrows indicate bone with metastatic tumors. F) Bioluminescence signals due to cancer cells and fluorescence of NPs, demonstrating localization of NPs into metastasized tumor mass. For the above colocalization study, both bioluminescence signals due to cancer cells and fluorescence signals due to NPs were captured using IVIS®. Bright spots seen next to the tumor in tibia (FIG. 4F, fluorescence signal) are due to localization of the injected NPs in lymph nodes and other tissues. Data are shown as mean±s.e.m., *P<0.05.
Figure 4:
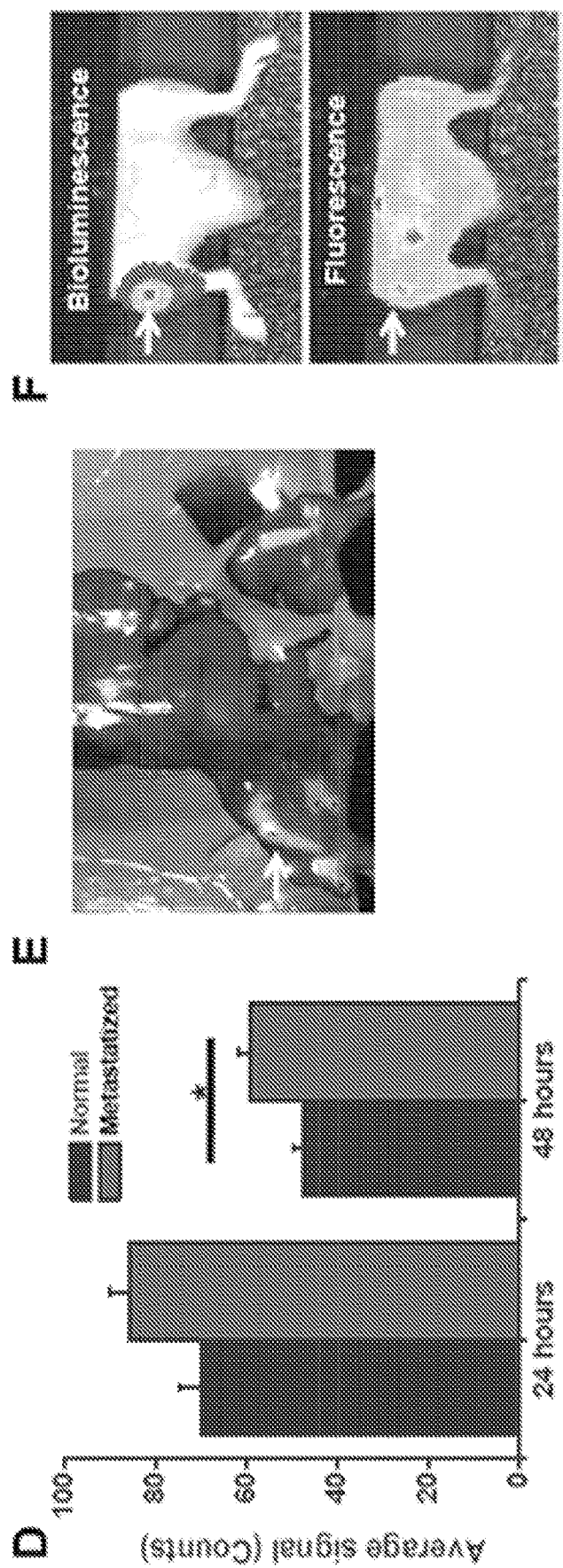

Bioluminescence and micro-CT images confirmed induction of intraosseous tumor in the lumen of the tibia within 1 week post inoculation of bone marrow with PC-3M-luc cells (FIG. 4A,B). The imaging data demonstrated that neutral NPs following IV administration show two-fold greater accumulation in the tibia with metastasis than in the normal contralateral tibia (FIG. 4C,D). Ex vivo imaging of the harvested bone from these animals further confirmed greater localization of neutral NPs in the metastasized tibia than in the normal contralateral tibia (FIG. 4E). In addition, co-localization of bioluminescence signal of cancer cells with fluorescence signal of NPs (FIG. 4F) indicated the delivery of neutral NPs to the tumor mass in the bone marrow.

Inhibition of Bone Metastasis with Paclitaxel-Loaded NPs.

Figure 7:
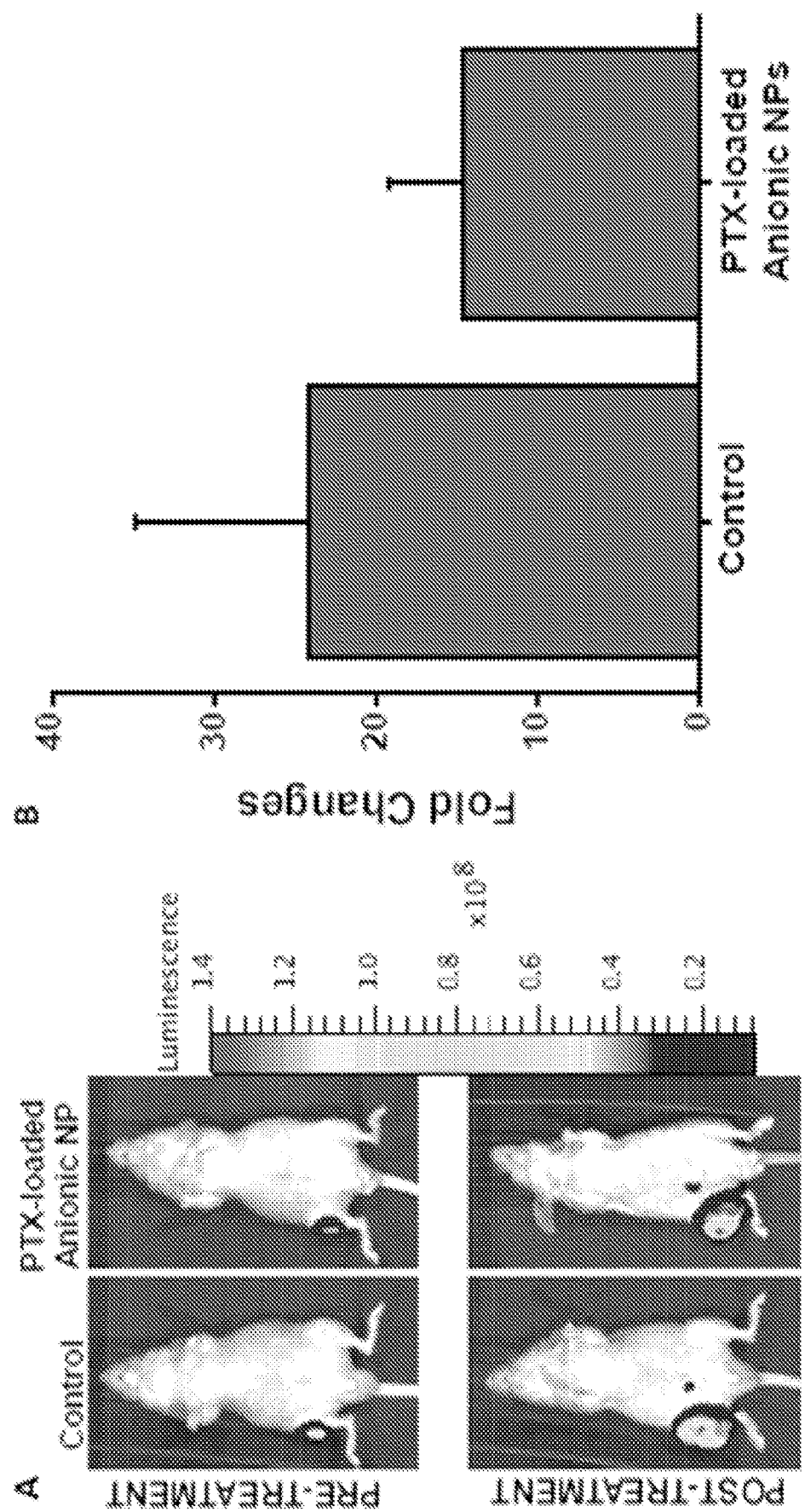
FIG. 7 shows results of inhibition of intraosseous tumor by PTX-loaded Anionic NPs. Changes in bioluminescence images (A) and fold changes in bioluminescence signal (B) in control and treated with PTX-NPs at 3 wks. In this case, each animal acted as its own control (signal at 7 day post-tumor inculcation was taken as baseline). There is no significant difference between bioluminescence signals from intraosseous tumors of mice treated with PTX-loaded anionic NPs compared to untreated controls at 3 wks post treatment. Data are shown as mean±s.e.m., P>Not Significant; n=4.

Bioluminescence imaging demonstrated slower progression of bone metastasis in the animals treated with PTX-NPs than with PTX-CrEL or saline control (FIG. 5A). Interestingly, the animals treated with PTX-CrEL showed relatively greater tumor progression than those receiving saline. Based on the bioluminescence signal intensity at 2 weeks post treatment, animals treated with PTX-NPs demonstrated 89% and 96% lower tumor burden than saline controls or those treated with PTXCrEL, respectively (P<0.05). At 3 weeks post treatment, animals that had received PTX-NPs still demonstrated a lower tumor burden: 61% and 143% lower than untreated controls or those treated with PTX-CrEL, respectively (FIG. 5A,B). Tumor burden, calculated from the weight difference between the limb with tumor and the contralateral normal limb at the end of the study (5 weeks post treatment), shows significantly lower tumor burden in animals treated with PTXNP than in untreated saline controls or the animals treated with PTX-CrEL (P<0.05) (FIG. 5C). Since anionic and cationic NPs have similar bone marrow uptake and retention (FIG. 3), we tested PTX-loaded anionic NPs for inhibition of bone metastasis. The data show insignificant difference in the bioluminescence signal in treated and saline control at the end of 3 weeks (FIG. 7). Analysis of the harvested tibia at 5 weeks post treatment using micro-CT showed no bone loss in the PTX-NP-treated animals, whereas the PTX-CrEL-treated animals showed >50% bone resorption, similar to the bone loss seen in the saline control animal (FIG. 5D). Animals treated with PTX-CrEL showed weight loss; in contrast, those treated with PTX-NPs gained weight, indicating there was no acute drug toxicity with PTX delivered encased in NPs (FIG. 5E). Animals in all groups showed weight loss at 5 weeks compared to their weights at 3 weeks, but those treated with PTX-CrEL showed greater weight loss than saline control or animals treated with PTX-NPs.

Figure 3:
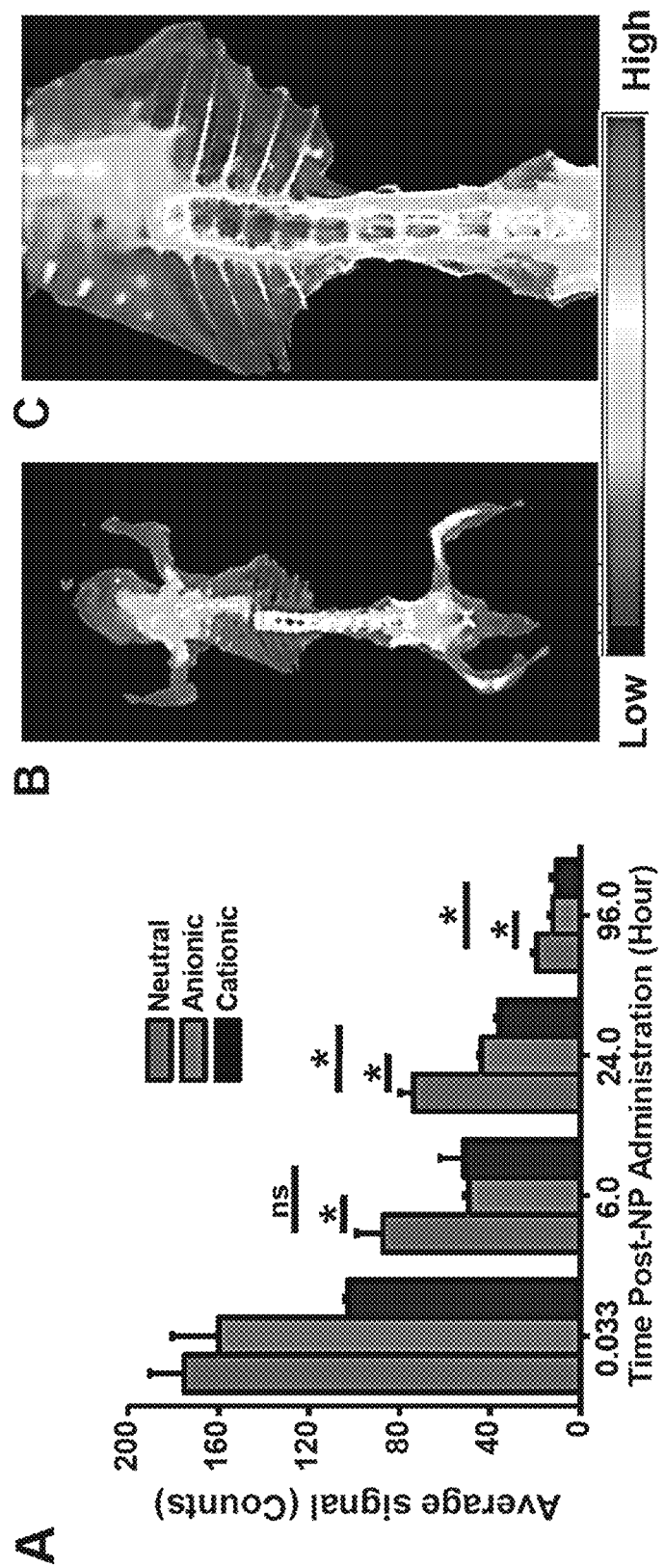
FIG. 3 shows the localization with NPs of different surface charge in bones. A) Quantification of fluorescence signals due to NP localization in tibia over time as measured using Maestro, demonstrating greater uptake and sustained retention of neutral NPs than of anionic or cationic NPs. B) Ventral view of skeleton of mouse injected with neutral NPs, showing NP localization in all bones, particularly pelvis, long bones, sternum, and vertebrae. C) Close-up view of the vertebral column shows greater NP localization in cervical than lumbar vertebrae. D) Image of the surgically resected tibia, showing localization of neutral NPs in marrow (arrow) but not in calcified bone. E) Flow cytometry analysis showing uptake of NPs by bone marrow cells. F) Quantification of the flow cytometry data shows that >90% of bone marrow cells internalize neutral NPs. Data are shown as mean±s.e.m., *P<0.05, ns=not significant; data shown in B to D at 24 hours post NP administration.
Figure 3:
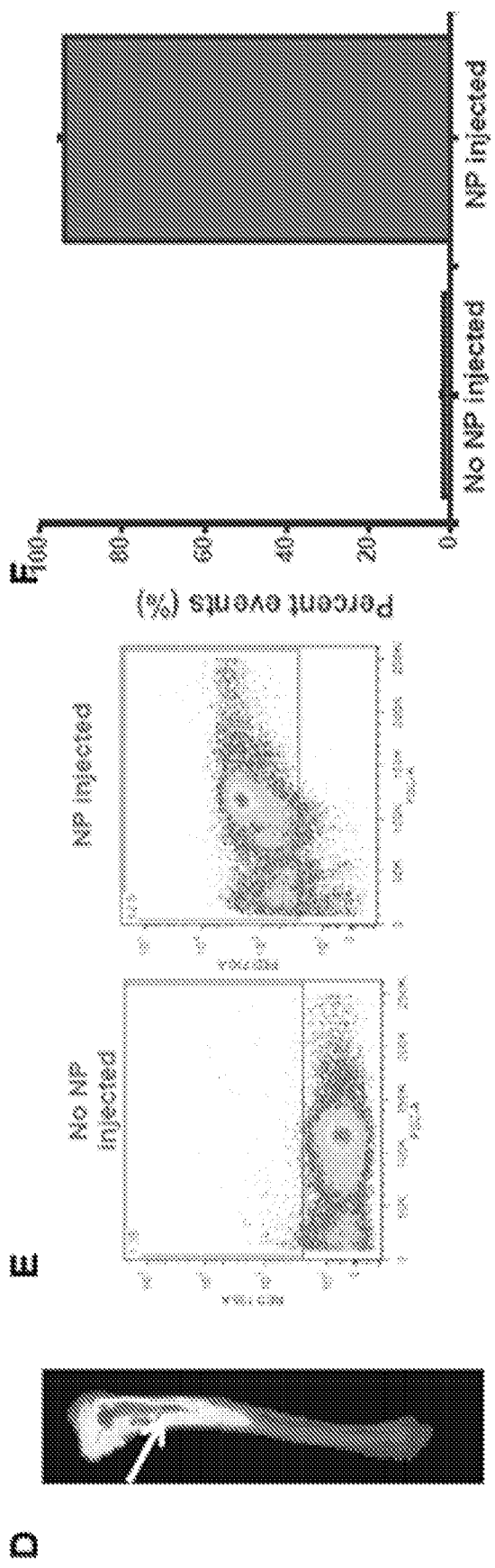

Progress in the field of cancer nanomedicine is evident from the entry of several NP-based therapies and an increasing number of ongoing clinical studies for treating different types of cancers [34, 35]. In general, the efficacy of NPs has been attributed to either better drug delivery directly to cancerous tissue and/or reduced toxicity compared with drugs alone. However, most of these approaches have been focused on treating primary soft-tissue, highly vascularized, solid tumors. Effective treatment for tumors that arise from advanced-stage cancer metastasis, the major cause of cancer-related mortality, still remains a challenge. In this example, the sinusoidal nature of blood-bone marrow capillaries was explored to deliver NPs to the marrow and it was found that neutral PTX-NPs are demonstrably effective in slowing the progression of bone metastasis and inhibiting bone loss in an intraosseous model of bone metastasis. Since neutral NPs have a prolonged circulation time compared with anionic and cationic NPs and since they are also smaller than the opening of the intercellular clefts of bone marrow endothelial cells, neutral NPs are more effective in localizing in the marrow (FIG. 3).

Neutral NPs have been reported to have a lower propensity to interact with proteins, which could be the reason for their relatively longer time in the circulation than charged NPs [36]. Furthermore, while the present invention is not limited to any particular mechanism, and an understanding of the mechanism is not necessary to practice the invention, it believed that surface-associated PVA, which is present in greater amounts on neutral NPs than on anionic or cationic NPs, could have played a role in sustaining the retention time of the NPs in the bloodstream.

PVA is a copolymer comprising both hydrophobic and hydrophilic portions. A hydrophobic polyvinyl acetate segment integrates within the PLGA-NP matrix, whereas a hydrophilic segment forms an outer corona that could also reduce opsonization [36]. It has been previously shown that a significant fraction of PVA remains associated with the NPs over several days when incubated in PBS at 37° C. [37]. This finding means that the NPs' surface composition would be maintained for a period of time following their IV injection, which is important, since the surface characteristics of the NPs determine their bio-distribution.

The general strategy used to keep NPs in the circulation is to prevent their recognition by circulating monocytes and their subsequent clearance by the organs of the reticuloendothelial system (RES), particularly the liver and spleen. In this example, it was found that at 2 minutes post NP administration, the liver signal due to NPs, particularly for neutral NPs, drops over time (FIG. 2A). This drop suggests that the major fraction of these NPs become contained in the vascular compartment of the liver and are not taken up by Kupffer cells or hepatocytes. The liver receives 30% of cardiac output. Therefore, the initial high fluorescence signal seen in the liver could be due to the NPs carried with the blood flow to the liver [38].

Generally, NPs taken up by Kupffer cells degrade slowly, whereas those taken up by hepatocytes are excreted through the hepatic biliary duct into the gut. This process is known to occur more rapidly for cationic than anionic NPs [39] but has not yet been reported for neutral NPs. The relatively more rapid drop in the liver signal seen in this example in animals injected with neutral NPs than cationic or anionic NPs suggests that neutral NPs are better at escaping uptake by Kupffer cells or hepatocytes than anionic or cationic NPs (FIG. 2A,B). For delivery to the bone marrow, it is important that NPs escape sequestering by the liver so that they remain in the circulation long enough to pass through the sinusoidal capillaries in the marrow.

The neutral NPs in this example seem to have avoided sequestering by the liver through their reduced opsonization, thus preventing their uptake by circulating monocytes and subsequent clearance by the organs of the RES, such as liver and spleen. Furthermore, the size of neutral NPs (~150 nm hydrodynamic diameter, 112 nm in the dry state, measured using AFM) is greater than the opening of the fenestrations (~75 nm) in the liver sinusoidal endothelial cell lining [40] but smaller than those in the bone marrow endothelial cell capillaries (170 nm) [16, 17, 41]. In this regard, neutral NPs appear to achieve the above balance in two ways: first, by escaping the liver and remaining in the circulation, but then (following their passage through the bone's sinusoidal capillaries) becoming sequestered in the marrow because of the marrow's comparatively sluggish blood flow [42] (FIGS. 2B and 3A). Despite a quite uniform size distribution (Table 1), a fraction of the smaller NPs present in the formulation could have passed through the sinusoidal capillaries of the liver. Thus, hepatic uptake of these NPs could not be completely prevented but might be further minimized by controlling particle size within a certain narrow range.

Conventionally, NPs are modified with hydrophilic polymers such as polyethylene glycol (PEG; PEGylated NPs) or pluronics to extend their time in the circulation. This is the approach commonly explored, via the enhanced permeation and retention (EPR) effect, for delivery of anticancer therapeutics to vascularized primary tumors [43]. However, PEGylated/pluronic modified NPs cannot effectively extravasate into the bone marrow [44]. Several studies have reported that uptake of these NPs into bone marrow remains negligible [45]. It is possible that steric hindrance due to the surface-associated PEG/pluronic could have prevented extravasation of these NPs into bone marrow. Considerable data in the recent literature suggest that PEGylation increases the circulation time of NPs yet has the concomitant negative effect of reducing cellular and tissue uptake of NPs. This steric hindrance is thought to be caused by protruding hydrated PEG chains at the NP surface [36, 46]. Similarly, while the present invention is not limited to any particular mechanism, we speculate that rather than extravasating efficiently into bone marrow due to their reduced interactions with the marrow's cells and tissues, PEGylated NPs remain in the blood circulation.

In addition to charge, the size of NPs is known to influence their localization in bone marrow. The data in this Example show that neutral NPs have about a 7-fold greater localization in bone marrow than larger NPs (hydrodynamic diameter ~150 nm vs. ~320 nm), signifying that the openings in the intercellular clefts between endothelial cells lining the bone marrow, which are ~170 nm, regulate the delivery of NPs to the bone marrow [16, 17]. Currently, patients with bone metastasis are treated with bisphosphonates to reduce the risk of deleterious skeleton-related events and to ameliorate bone pain, as bisphosphonates can inhibit bone resorption [47]. Some studies have also reported that bisphosphonates indirectly slow the progression of bone metastasis [48] by inhibiting osteoclast-mediated bone resorption and thereby the release of growth factors necessary to promote cancer cell growth and differentiation and subsequent tumor formation in bone [49]. However, a recent review of data from different clinical studies shows no statistically significant improvement in survival of bisphosphonate-treated patients compared with placebo controls [50]. Furthermore, bisphosphonates show dose-limiting toxicities, with chronic use, they cause osteonecrosis of the jaws, considered to be a consequence of their effect on circulating endothelial progenitor cells, interfering in the normal process of angiogenesis and vasculogenesis required to maintain healthy tissue [51].

Figure 5:
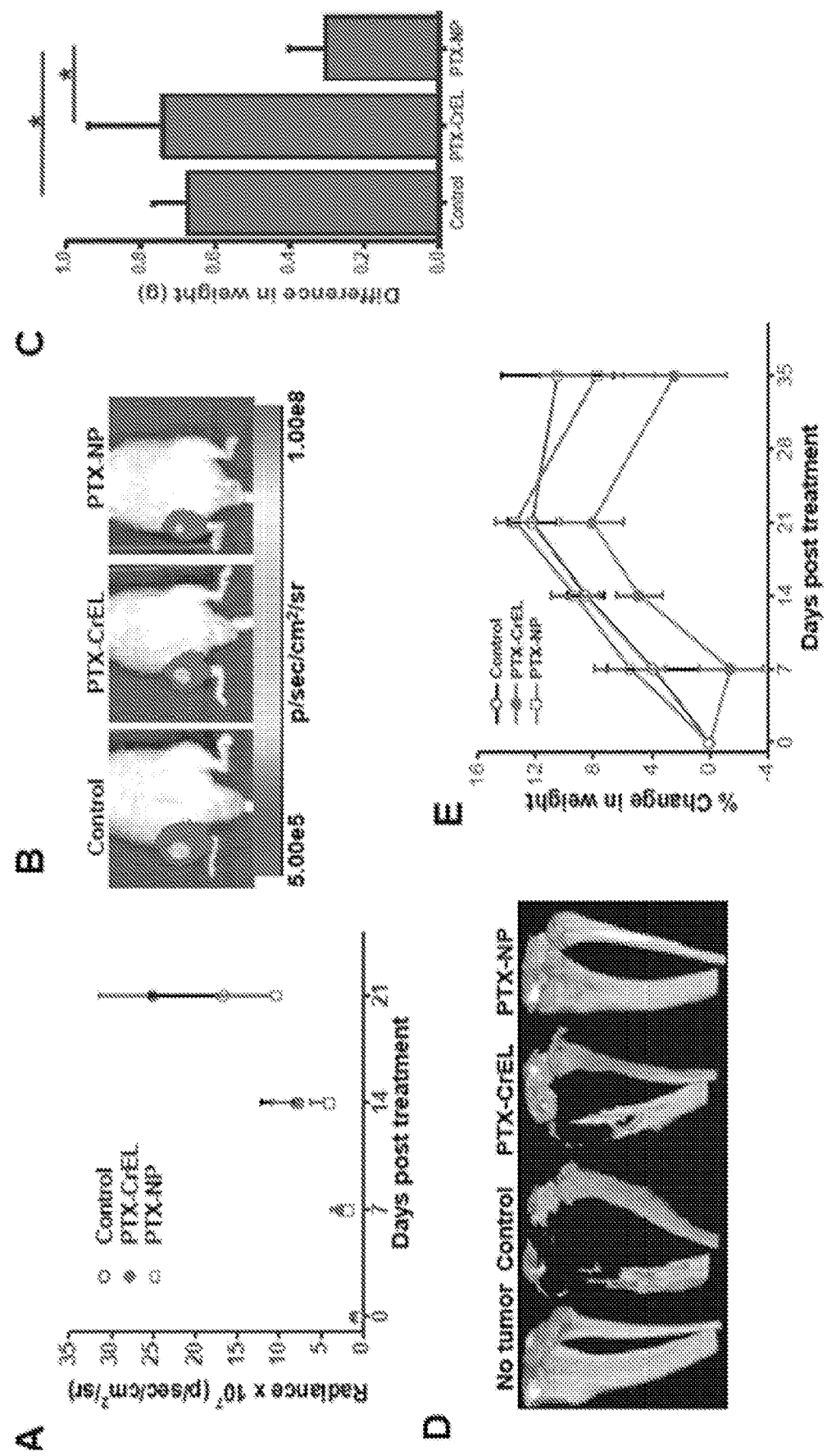
FIG. 5 shows efficacy of paclitaxel-loaded neutral NPs in a bone metastasis model. A) Change in bioluminescence signals due to cancer cells in bone as measured using IVIS® during 3 weeks post treatment. *P<0.05 at 2 weeks between PTX-NPs and other groups; *P<0.05 between PTX-NPs and PTX-CrEL at 3 weeks; **no statistical significance between PTX-NPs and saline at 3 weeks days. B) Representative bioluminescence images of the bone with tumor captured using IVIS® at 3 weeks post treatment. C) Tumor burden at 5 weeks post treatment, determined by subtracting the weight of the normal contralateral leg from that of the leg with tumor. D) Representative micro-CT of tibias of mice from different groups at 5 weeks post treatment. Animals treated with PTX-NPs showed no bone loss. E) Changes in body weight of animals post treatment. Data are shown as mean±s.e.m., *P<0.05 PTX-NPs and control vs. PTX-CrEL; Not significant, PTX-NPs vs. control, n=5-6.

This example has shown that NPs localize to and are retained in marrow, where bone metastasis initiates and progresses, rather than to bone itself. Furthermore, the increased accumulation of NPs in bone that has been invaded by cancer compared with normal bone could be due to increased permeability of the blood-bone microvasculature as a result of tumor growth. Since NPs also localize into the metastatic tumor mass, the therapy is effective in suppressing the progression of bone metastasis (FIG. 5). One important finding of this example was that a single-dose IV injection of neutral PTX-NPs prevented bone loss (FIG. 5D), suggesting the NPs' efficacy in delivering drug to marrow to prevent invasion of PC-3 cells in bone matrix.

PTX is known to inhibit receptor activator of nuclear factor-kappa B ligand (RANKL)-induced osteoclastogenesis by causing mitotic arrest of osteoclastic precursor cells, thus inhibiting the progression of bone metastasis to pathological osteolysis [52]. Bone loss is a significant clinical issue when prostate cancer metastasizes to bone.

PLGA-based NPs typically demonstrate a triphasic release profile: the first release phase is mediated via diffusion of the drug at the interface, followed by a second, steady-release phase during which an insignificant amount of the encapsulated drug is released, and the third phase, in which the polymer matrix degrades, releasing the remaining encapsulated drug. Thus it appears that a considerable fraction of PTX is still entrapped within the NPs. Previously, it was reported that a complete release of PTX from a similar formulation of PLGA-based NPs occurring over ~90 days in vitro [53]. Therefore, modulating the drug-release rate from NPs to synchronize it with the retention of NPs in the bone metastatic site, which is ~96 hrs (FIG. 3A), should further improve the outcome.

Most in vivo efficacy studies use repeated dosing of anticancer drugs over a short period of time, which provides a sustained exposure of cancer cells to chemotherapy. In this example, animals received a single dose of PTX-CrEL, and it is possible that only a subtherapeutic level of PTX reached the metastatic sites in bone, stimulating the proliferation of cancer cells, as some teams have reported [54, 55]. Unlike PTX-CrEL (PTX release of 70% in 4 hours and 100% in 12 hours) [56], PTX-NPs provided a continuous localized dose of PTX (~0.7% per day), thus providing the comparison between fast- and sustained-release formulations of PTX on their efficacy. NP albumin-bound (nab) PTX, despite having smaller particle size (~130 nm) than the openings of the bone marrow capillary fenestrations (~170 nm), has in fact been shown to increase the incidence of metastasis, including to bones, in an animal model of breast cancer metastasis [57]. Similar to PTX-CrEL, nab-PTX is a fast-release drug formulation and has a clearance profile similar to that of PTX-CrEL [58].

The data in this example with PTX-CrEL and the findings with nab-PTX thus signify the importance of sustained drug delivery to inhibit the progression of bone metastasis. Among the drawbacks of chemotherapy are the severe side effects seen in normal tissues, at times presenting as myelosuppression and weight loss [59, 60]. In this example study, we did not see acute toxicity with PTX-NPs, which could be the combined effect of sustained release, of only a fraction of the encapsulated PTX being released from NPs during the experimental time period, and/or of altered biodistribution of PTX with NPs, which other investigators have also reported [61, 62].

We have also shown that, in addition to tibia, neutral NPs localize in the pelvis and vertebrae, which are common sites for metastasis in prostate and breast cancers. At later stages of prostate cancer, there is gross metastasis to the bones involving the ribs, sternum, and long bones [4, 63, 64]. Since neutral NPs localize to these sites (FIGS. 3B and C), they could be employed for drug delivery to control late-stage bone metastasis. Although prostate cancer bone metastasis usually is osteoblastic and that of breast cancer is osteolytic, the PC-3M-luc cells used in our study were osteolytic [65]. All cancer types are contemplated with the present invention. Prolonged circulation time is considered critical to give the NPs sufficient time to localize into soft-tissue tumors, as NPs often extravasate through the leaky tumor vasculature due to the EPR effect [66]. Hence, neutral NPs could very well be effective in treating both primary tumors and those that have metastasized to bone.

EXEMPLARY CONCLUSIONS

This example has demonstrated that neutral NPs localize in bone marrow more than anionic or cationic NPs and that PTX-loaded NPs with a neutral surface charge are effective in slowing the progression of bone tumor metastasis, reducing tumor burden, and inhibiting bone loss. Skeletal complications from bone metastases are associated with many consequences, including a diminished quality of life, increased medical costs, impaired mobility, and a negative impact on survival. Hence, an effective drug-delivery strategy to bone marrow could have significantly broader therapeutic implications in treating bone metastasis, which otherwise is very difficult to treat.

REFERENCES FOR EXAMPLE 1

[1] Coleman, Cancer Treat Rev, 27 (2001) 165-176.
[2] Morrissey, J Cell Biochem, 101 (2007) 873-886.
[3] Kuru, et al., Singapore medical journal, 49 (2008) 904-911.
[4] Berruti, et al., J Urol, 164 (2000) 1248-1253.

[5] Ramanlal Chaudhari, J Control Release, 158 (2012) 470-478.
[6] El-Mabhouh, et al., Oncol Res, 19 (2011) 287-295.
[7] Thamake, et al., Biomaterials, 33 (2012) 7164-7173.
[8] Hirabayashi, et al., Clin Pharmacokinet, 42 (2003) 1319-1330.
[9] Mann, et al., Adv Mater, 23 (2011) H278-282.
[10] Wang, et al., J Drug Target, 18 (2010) 611-626.
[11] Swami, et al., Proc Natl Acad Sci USA, 111 (2014) 10287-10292.
[12] Brannon-Peppas, et al., Adv Drug Deliv Rev, 56 (2004) 1649-1659.
[13] Davis, et al., Nat Rev Drug Discov, 7 (2008) 771-782.
[14] Cabral, et al., Proc Natl Acad Sci USA, 110 (2013) 11397-11402.
[15] Hrkach, et al., Sci Transl Med, 4 (2012) 128ra139.
[16] H. Sarin, J Angiogenes Res, 2 (2010) 14.
[17] Taichman, Blood, 105 (2005) 2631-2639.
[18] Arvizo, et al., PLoS ONE, 6 (2011) e24374.
[19] Asati, et al., ACS Nano, 4 (2010) 5321-5331.
[20] Hirsch, et al., Nanoscale, 5 (2013) 3723-3732.
[21] Sharma et al., Cancer Lett, 334 (2013) 228-236.
[22] Adjei, et al., Nanomedicine (Lond), 9 (2014) 267-278.
[23] Panyam, et al., Pharm Res, 20 (2003) 212-220.
[24] Panyam, et al., et al., Mol Pharmaceutics, 1 (2004) 77-84.
[25] Panyam, et al., FASEB J, 16 (2002) 1217-1226.
[26] Sahoo, et al., J Control Rel, 82 (2002) 105-114.
[27] Foy, et al., ACS Nano, 4 (2010) 5217-5224.
[28] Gordon, et al., Nat Rev Immunol, 5 (2005) 953-964.
[29] Park, et al., Curr Protoc Pharmacol, Ch. 14, Unit 14.15 (2001).
[30] Kim, et al., Cancer Res, 65 (2005) 3707-3715.
[31] Kim, et al., J Natl Cancer Inst, 98 (2006) 783-793.
[32] Panyam, et al., J Pharm Sci, 93 (2004) 1804-1814.
[33] Ballou, et al., Bioconjug Chem, 15 (2004) 79-86.
[34] Damascelli et al., Cancer, 92 (2001) 2592-2602.
[35] Harries, et al., J Clin Oncol, 23 (2005) 7768-7771.
[36] Owens, Int J Pharm, 307 (2006) 93-102.
[37] Panyam et al., J Control Release, 92 (2003) 173-187.
[38] Wynne, et al., Hepatology, 9 (1989) 297-301.
[39] Souris, et al., Biomaterials, 31 (2010) 5564-5574.
[40] Warren et al., Microcirculation, 17 (2010) 32-38.
[41] Moghimi, Adv Drug Deliv Rev, 17 (1995) 61-73.
[42] Kahn, et al., Blood, 83 (1994) 958-963.
[43] Cabral, et al., J Control Release, 190 (2014) 465-76.
[44] Kwon, et al., J Control Release, 164 (2012) 108-114.
[45] Vandorpe, et al., Biomaterials, 18 (1997) 1147-1152.
[46] Oh, et al., ACS Nano, 5 (2011) 6434-6448.
[47] Talreja, Cancer Manag Res, 4 (2012) 287-297.
[48] Boissier, et al., Cancer Res, 60 (2000) 2949-2954.
[49] Green, et al., Am J Clin Oncol, 25(6 Suppl 1) (2002) S3-9.
[50] Lopez-Olivo, et al., Support Care Cancer, 20 (2012) 2985-2998.
[51] Allegra, et al., Acta Haematol, 124 (2010) 79-85.
[52] Ang et al., J Cell Biochem, 113 (2012) 946-955.
[53] Sahoo, et al., Int J Cancer, 112 (2004) 335-340.
[54] Vassileva, et al., Mol Cancer Ther, 7 (2008) 630-637.
[55] Vassileva, et al., Br J Cancer, 99 (2008) 2037-2043.
[56] Nie, et al., Int J Nanomedicine, 6 (2011) 151-166.
[57] Ernsting, et al., J Control Release, 162 (2012) 575-581.
[58] Desai, et al., ClinCancer Res, 12 (2006) 1317-1324.
[59] Karapanagiotou, et al., Clin Cancer Res, 18 (2012) 2080-2089.
[60] Green et al., J Pharm Sci, 100 (2011) 4205-4209.
[61] Farokhzad et al, Proc Natl Acad Sci USA, 103 (2006) 6315-6320.
[62] Kalaria et al., Pharm Res, 26 (2009) 492-501.
[63] Suzuki et al., Prostate, 25 (1994) 141-146.
[64] Mundy, Nat Rev Cancer, 2 (2002) 584-593.
[65] Olechnowicz, Cancer Res, 74 (2014) 1625-1631.
[66] Maeda, Adv Enzyme Regul, 41 (2001) 189-207.

Example 2

Inhibition of Bone Loss with Surface-Modulated, Docetaxel-Loaded Nanoparticles

This example evaluated docetaxel (TXT)-loaded nanoparticles (TXT-NPs) to determine cytotoxic effect of TXT-NPs in prostate cancer cell lines in vitro, and in an in vivo model.

Formulating TXT-NPs

In this Example, the efficacy of TXT-NPs was evaluated, as TXT is generally the preferred drug used for treating prostate cancer because it is more potent than PTX. Hence, we began designing and developing formulation of NPs loaded with TXT using the same protocol used for PTX (Example 1 above), considering that both the drugs have similar chemical structures and physical properties, particularly their hydrophobicity based on octanol-water partition coefficient. It was found that the PLGA polymer used for making PTX-NPs was not compatible with TXT, as there was phase separation of the drug from the polymer, resulting in TXT crystallization and large aggregate formation during the NP formation. This led to the study to determine solid-state solubility of TXT in different PLGA-based polymers in order to identify a polymer or polymers that do not cause phase separation of the drug. For this example, polymer and drug solutions in chloroform at different % of drug to polymer were casted into films on glass slides. Following solvent evaporation of chloroform in a chemical hood overnight, the casted films were observed under a light microscope. Phase separation was clearly evident from crystallization of the drug in the polymer film whereas the films were homogeneous when there was no phase separation.

As shown in Table 2, PTX and TXT have quite different solid-state solubility profile in polymers.

TABLE 2

Solid State Solubility of PTX and TXT in Polymers

| Inherent viscosity (dL/g) | Lactide/ Glycolide | Phase Separation: Paclitaxel Concentration (w/w %) | | | | | Phase Separation: Docetaxel Concentration (w/w %) | | | | |
|---|---|---|---|---|---|---|---|---|---|---|---|
| | | 1% | 5% | 10% | 15% | 20% | 1% | 5% | 10% | 15% | 20% |
| 1.24 | 50/50 | + | + | + | + | + | + | + | + | + | + |
| 1.15 | 50/50 | + | + | + | + | + | + | + | + | + | + |
| 0.95-1.20 | 50/50 | − | − | − | − | + | − | − | − | − | + |
| 0.76-0.94 | 50/50 | + | + | + | + | + | + | + | + | + | + |
| 0.87 | 50/50 | + | + | + | + | + | + | + | + | + | + |

TABLE 2-continued

Solid State Solubility of PTX and TXT in Polymers

| Inherent viscosity (dL/g) | Lactide/ Glycolide | Phase Separation: Paclitaxel Concentration (w/w %) | | | | | Phase Separation: Docetaxel Concentration (w/w %) | | | | | |
|---|---|---|---|---|---|---|---|---|---|---|---|---|
| | | 1% | 5% | 10% | 15% | 20% | 1% | 5% | 10% | 15% | 20% | |
| 0.69 | 50/50 | + | + | + | + | + | − | − | − | − | + | |
| 0.69 | 50/50 | + | + | + | + | + | + | + | + | + | + | |
| 0.67 | 65/35 | + | + | + | + | + | − | + | + | + | + | |
| 0.64 | 75/25 | + | + | + | + | + | + | + | + | + | + | |
| 0.64 | 65/35 | + | + | + | + | + | + | + | + | + | + | |
| 0.63 | 85/15 | + | + | + | + | + | + | + | + | + | + | |
| 0.55-0.75 | 50/50 | − | − | − | − | − | + | + | + | + | + | Carbohydrate end Group |
| 0.26-0.54 | 50/50 | − | − | − | − | − | + | + | + | + | + | Ester Terminated |
| 0.39 | 50/50 | + | + | + | + | + | − | − | − | − | − | |
| 0.18 | 75/25 | + | + | + | + | + | + | + | + | + | + | |
| 0.16 | 50/50 | + | + | + | + | + | − | − | − | − | − | |

+ve: Phase separation
−ve: No phase separation

There are polymers, which showed phase separation either for PTX or TXT but there are few polymers that did not show phase separation for both the drugs. The data also show examples of the optimal amount of drug that one can incorporate into polymers without phase separation. We confirmed the solid-state solubility data by formulating NPs with the respective polymers and found the polymers that show no phase separation resulted in formulation of NPs without drug crystals and vice versa (i.e. the polymers that show phase separation lead to drug crystallization and aggregate formation). Based on the solid-state data, we selected PLGA 50:50, inherent viscosity 0.69 for the formulation of TXT-NPs (Table 2, marked in bold).

The polymers, PLGA with inherent viscosity of 0.39 and 0.16 (50:50 lactide to glycolide ratio) which also did not show phase separation were also tested but resulted in lower drug encapsulation efficiency than those formulated with inherent viscosity of 0.69. One the issues that with the PTX-NPs was the slow release of the encapsulated drug. In order to facilitate the release of TXT, we incorporated a pore-forming agent, dimethyl tartaric acid (DMT, 10% w/w) into the formulation.

Cytotoxicity Study In Vitro in Prostate Cancer Cells

In order to confirm the efficacy of TXT NPs, we determined IC50 of the drug and drug encapsulated in NPs in PC-3 and DU145 cells. The data show that the drug is quite effective as evident from the low IC50 values whether it is encapsulated or not (Table 4).

TABLE 4

Cytotoxicity of TXT and TXT-NPs

| Cell-line | End point | TXT (ng/mL) | $IC_{50}$ | $IC_{75}$ | $IC_{90}$ |
|---|---|---|---|---|---|
| PC3 | 3 day | TXT Soln. | 2.5 ± 0.05 | 3.8 ± 0.03 | 6.31 ± 0.17 |
| | | TXT-NPs | 2.6 ± 0.04 | 4.9 ± 0.09 | 13.8 ± 0.3 |
| | 5 day | TXT Soln. | 1.6 ± 0.01 | 2.5 ± 0.02 | 5 ± 0.07 |
| | | TXT-NPs | 2 ± 0.03 | 4 ± 0.08 | 15.36 ± 0.7 |
| | 7 day | TXT Soln. | 1.6 ± 0.01 | 2.5 ± 0.01 | 4.2 ± 0.08 |
| | | TXT-NPs | 2 ± 0.01 | 3.4 ± 0.02 | 7.03 ± 0.23 |
| DU145 | 5 day | TXT Soln. | 1.5 ± 0.04 | 1.9 ± 0.03 | 2.40 ± 0.02 |
| | | TXT-NPs | 1.6 ± 0.03 | 2.2 ± 0.03 | 3.1 ± 0.04 |

Evaluation of TXT-NPs In Vivo

Figure 8:
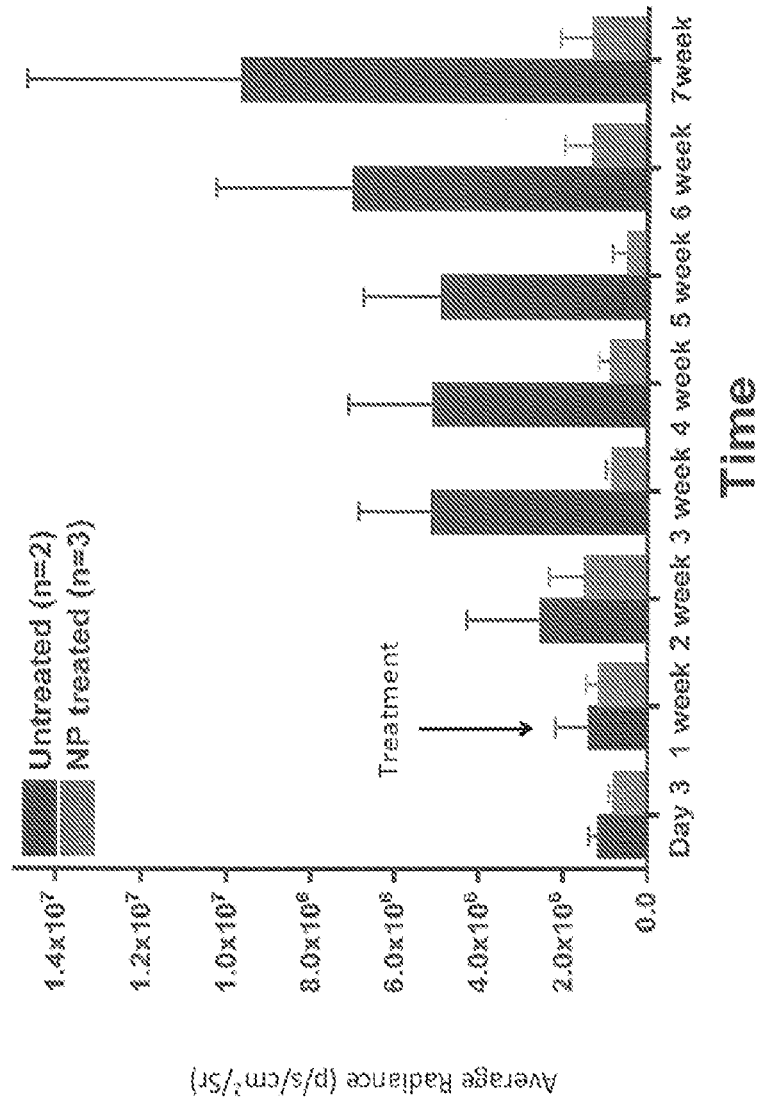
FIG. 8 shows results of inhibition of progression of bone metastasis in intraosseous model of prostate cancer. PC-3 Luc cells (5×10$^5$ in 20 μL) were injected into the lumen of the right tibia of nude mice. Change in bioluminescence signal intensity due to cancer cells was measured. The treatment (12 mg/kg docetaxel, TXT equivalent dose TXT-NPs) was administered through tail vein at one-week post-tumor inoculation whereas controlled group did not receive any treatment.

TXT-NPs were tested for their efficacy in a small number of animals to ensure their efficacy in inhibiting the progression of bone metastasis. For this, an intraosseous model of prostate cancer was used where PC-3-Luc cells were injected into the tibia. PC-3 Luc cells ($5 \times 10^5$ in 20 μL) were injected into the lumen of the right tibia of nude mice. Change in bioluminescence signal intensity was measured. The treatment (12 mg/kg TXT equivalent dose TXT-NPs) was administered through tail vein at one-week post-tumor inoculation whereas controlled group did not receive any treatment. The data shows the inhibition of bone metastasis following a single-dose intravenous injection of TXT-NPs as compared to untreated control (FIG. 8). These results further shows that although TXT and PTX have similar structures and physical properties, they have different solid-state solubility with polymers which significantly impact the selection of polymer for formulating NPs for each drug. These results also show that formulated TXT-NPs are effective in vitro in cell culture and in vivo in bone metastasis model of prostate cancer. These results shows that a single-dose intravenous injection of TXT-NPs is effective in inhibiting the progression of bone metastasis.

REFERENCES

1. Coleman, Metastatic bone disease: clinical features, pathophysiology and treatment strategies. Cancer Treat Rev 27, 165-176 (2001).
2. Morrissey, et al., The role of tumor microenvironment in prostate cancer bone metastasis. J Cell Biochem 101, 873-886 (2007).
3. Bubendorf, et al. Metastatic patterns of prostate cancer: an autopsy study of 1,589 patients. Hum Pathol 31, 578-583 (2000).
4. Berruti, et al. Incidence of skeletal complications in patients with bone metastatic prostate cancer and hormone refractory disease: predictive role of bone resorption and formation markers evaluated at baseline. J Urol 164, 1248-1253 (2000).
5. Siegel, et al., Cancer statistics, 2013. CA-Cancer J Clin 63, 11-30 (2013).
6. Kuru, et al. Prognostic factors for survival in breast cancer patients who developed distant metastasis subsequent to definitive surgery. Singapore Med J 49, 904-911 (2008).
7. Berruti, et al. Incidence of skeletal complications in patients with bone metastatic prostate cancer and hormone refractory disease: Predictive role of bone resorption and formation markers evaluated at baseline. J Urol 164, 1248-1253 (2000).
8. Ramanlal Chaudhari, K., et al. Bone metastasis targeting: a novel approach to reach bone using Zoledronate anchored PLGA nanoparticle as carrier system loaded with Docetaxel. J Control Release 158, 470-478 (2012).
9. Body, et al., Targeting bone metastases in prostate cancer: improving clinical outcome. Nat Rev Urol 12, 340-356 (2015).
10. Casas, A., Llombart, A. & Martin, M. Denosumab for the treatment of bone metastases in advanced breast cancer. Breast 22, 585-592 (2013).
11. Drooger, J. C., van der Padt, A., Sleijfer, S. & Jager, A. Denosumab in breast cancer treatment. Eur J Pharmacol 717, 12-19 (2013).
12. Nangia, J. R., Ma, J. D., Nguyen, C. M., Mendes, M. A. & Trivedi, M. V. Denosumab for treatment of breast cancer bone metastases and beyond. Expert Opin Biol Ther 12, 491-501 (2012).
13. Miller, R. E., et al. RANK ligand inhibition plus docetaxel improves survival and reduces tumor burden in a murine model of prostate cancer bone metastasis. Mol Cancer Ther 7, 2160-2169 (2008).
14. Yuasa, T., Yamamoto, S., Urakami, S., Fukui, I. & Yonese, J. Denosumab: a new option in the treatment of bone metastases from urological cancers. Onco Targets Ther 5, 221-229 (2012).
15. Bienz, M. & Saad, F. Androgen-deprivation therapy and bone loss in prostate cancer patients: a clinical review. Bonekey Rep 4, 716 (2015).
16. Tsourdi, E., Rachner, T. D., Rauner, M., Hamann, C. & Hofbauer, L. C. Denosumab for bone diseases: translating bone biology into targeted therapy. Eur J Endocrinol 165, 833-840 (2011).
17. Matsuo, K. & Irie, N. Osteoclast-osteoblast communication. Arch Biochem Biophys 473, 201-209 (2008).
18. Guise, T. A., et al. Basic mechanisms responsible for osteolytic and osteoblastic bone metastases. Clin Cancer Res 12, 6213s-6216s (2006).
19. Keller, E. T. & Brown, J. Prostate cancer bone metastases promote both osteolytic and osteoblastic activity. J Cell Biochem 91, 718-729 (2004).
20. Talreja, D. B. Importance of antiresorptive therapies for patients with bone metastases from solid tumors. Cancer Manag Res 4, 287-297 (2012).
21. Boissier, S., et al. Bisphosphonates inhibit breast and prostate carcinoma cell invasion, an early event in the formation of bone metastases. Cancer Res 60, 2949-2954 (2000).
22. Green, J. R. & Clezardin, P. Mechanisms of bisphosphonate effects on osteoclasts, tumor cell growth, and metastasis. Am J Clin Oncol 25, S3-9 (2002).
23. Lopez-Olivo, M. A., et al. Bisphosphonates in the treatment of patients with lung cancer and metastatic bone disease: a systematic review and meta-analysis. Supportive Care Cancer 20, 2985-2998 (2012).
24. Allegra, A., et al. Bisphosphonates induce apoptosis of circulating endothelial cells in multiple myeloma patients and in subjects with bisphosphonate-induced osteonecrosis of the jaws. Acta Haematol 124, 79-85 (2010).
25. Thavarajah, N., et al. Patterns of practice in the prescription of palliative radiotherapy for the treatment of bone metastases at the Rapid Response Radiotherapy Program between 2005 and 2012. Curr Oncol 20, e396-405 (2013).
26. Mackiewicz-Wysocka, M., Pankowska, M. & Wysocki, P. J. Progress in the treatment of bone metastases in cancer patients. Expert Opin Investig Drugs 21, 785-795 (2012).
27. Damascelli, B., et al. Intraarterial chemotherapy with polyoxyethylated castor oil free paclitaxel, incorporated in albumin nanoparticles (ABI-007). Cancer 92, 2592-2602 (2001).
28. Harries, M., Ellis, P. & Harper, P. Nanoparticle albumin-bound paclitaxel for metastatic breast cancer. J Clin Oncol 23, 7768-7771 (2005).
29. Brannon-Peppas, L. & Blanchette, J. O. Nanoparticle and targeted systems for cancer therapy. Adv Drug Deliv Rev 56, 1649-1659 (2004).
30. Davis, M. E., Chen, Z. G. & Shin, D. M. Nanoparticle therapeutics: an emerging treatment modality for cancer. Nat Rev Drug Discov 7, 771-782 (2008).
31. Cabral, H., et al. Targeted therapy of spontaneous murine pancreatic tumors by polymeric micelles prolongs survival and prevents peritoneal metastasis. Proc Natl Acad Sci USA 110, 11397-11402 (2013).
32. Hrkach, J., et al. Preclinical development and clinical translation of a PSMA-targeted docetaxel nanoparticle with a differentiated pharmacological profile. Sci Transl Med 4, 128ra139 (2012).
33. El-Mabhouh, A. A., et al. A conjugate of gemcitabine with bisphosphonate (Gem/BP) shows potential as a targeted bone-specific therapeutic agent in an animal model of human breast cancer bone metastases. Oncol Res 19, 287-295 (2011).
34. Thamake, S. I., Raut, S. L., Gryczynski, Z., Ranjan, A. P. & Vishwanatha, J. K. Alendronate coated polylactic-co-glycolic acid (PLGA) nanoparticles for active targeting of metastatic breast cancer. Biomaterials 33, 7164-7173 (2012).
35. Hirabayashi, H. & Fujisaki, J. Bone-specific drug delivery systems: approaches via chemical modification of bone-seeking agents. Clin Pharmacokinet 42, 1319-1330 (2003).
36. Mann, A. P., et al. E-selectin-targeted porous silicon particle for nanoparticle delivery to the bone marrow. Adv Mater 23, H278-282 (2011).
37. Wang, G., Kucharski, C., Lin, X. & Uludag, H. Bisphosphonate-coated BSA nanoparticles lack bone targeting after systemic administration. J Drug Target 18, 611-626 (2010).
38. Swami, A., et al. Engineered nanomedicine for myeloma and bone microenvironment targeting. Proc Natl Acad Sci USA (2014).
39. Hirabayashi, H., et al. Relationship between physico-chemical and osteotropic properties of bisphosphonic derivatives: rational design for osteotropic drug delivery system (ODDS). Pharm Res 18, 646-651 (2001).
40. Price, P. A., et al. Discovery of a high molecular weight complex of calcium, phosphate, fetuin, and matrix γ-carboxyglutamic acid protein in the serum of etidronate-treated rats. J Biol Chem 277, 3926-3934 (2002).
41. Price, P. A. & Lim, J. E. The inhibition of calcium phosphate precipitation by fetuin is accompanied by the formation of a fetuin-mineral complex. J Biol Chem 278, 22144-22152 (2003).
42. Schroeder, A., et al. Treating metastatic cancer with nanotechnology. Nat Rev Cancer 12, 39-50 (2012).
43. Sarin, H. Physiologic upper limits of pore size of different blood capillary types and another perspective on the dual pore theory of microvascular permeability. J Angiogenes Res 2, 14 (2010).

44. Taichman, R. S. Blood and bone: two tissues whose fates are intertwined to create the hematopoietic stem-cell niche. Blood 105, 2631-2639 (2005).
45. Peter Klinken, S. Red blood cells. Int J Biochem Cell Biol 34, 1513-1518 (2002).
46. Sou, et al., Selective uptake of surface-modified phospholipid vesicles by bone marrow macrophages in vivo. Biomaterials 28, 2655-2666 (2007).
47. Warren, A., Cogger, V. C., Arias, I. M., McCuskey, R. S. & Le Couteur, D. G. Liver sinusoidal endothelial fenestrations in caveolin-1 knockout mice. Microcirculation 17, 32-38 (2010).
48. Cabral, H. & Kataoka, K. Progress of drug-loaded polymeric micelles into clinical studies. J Control Release (2014).
49. Kolate, A., et al. PEG—A versatile conjugating ligand for drugs and drug delivery systems. J Control Release 192C, 67-81 (2014).
50. Cu, Y. & Saltzman, W. M. Drug delivery: Stealth particles give mucus the slip. Nat Mater 8, 11-13 (2009).
51. Yang, M., et al. Vaginal Delivery of Paclitaxel via Nanoparticles with Non-Mucoadhesive Surfaces Suppresses Cervical Tumor Growth. Adv Healthc Mater 3, 1044-1052 (2014).
52. Kwon, I. K., Lee, S. C., Han, B. & Park, K. Analysis on the current status of targeted drug delivery to tumors. J Control Release 164, 108-114 (2012).
53. Vandorpe, J., et al. Long circulating biodegradable poly(phosphazene) nanoparticles surface modified with poly(phosphazene)-poly(ethylene oxide) copolymer. Biomaterials 18, 1147-1152 (1997).
54. Verhoef, J. J. F. & Anchordoquy, T. J. Questioning the use of PEGylation for drug delivery. Drug Deliv Transl Res 3, 499-503 (2013).
55. Lehtinen, J., et al. Analysis of cause of failure of new targeting peptide in PEGylated liposome: molecular modeling as rational design tool for nanomedicine. Eur J Pharm Sci 46, 121-130 (2012).
56. Hatakeyama, H., Akita, H. & Harashima, H. A multifunctional envelope type nano device (MEND) for gene delivery to tumours based on the EPR effect: a strategy for overcoming the PEG dilemma. Adv Drug Deliv Rev 63, 152-160 (2011).
57. Ernsting, M. J., et al. A docetaxel-carboxymethylcellulose nanoparticle outperforms the approved taxane nanoformulation, Abraxane, in mouse tumor models with significant control of metastases. J Control Release 162, 575-581 (2012).
58. Cheng, Z., Al Zaki, A., Hui, J. Z., Muzykantov, V. R. & Tsourkas, A. Multifunctional nanoparticles: cost versus benefit of adding targeting and imaging capabilities. Science 338, 903-910 (2012).
59. Arvizo, R. R., et al. Modulating pharmacokinetics, tumor uptake and biodistribution by engineered nanoparticles. PLoS ONE 6, e24374 (2011).
60. Asati, A., Santra, S., Kaittanis, C. & Perez, J. M. Surface-charge-dependent cell localization and cytotoxicity of cerium oxide nanoparticles. ACS Nano 4, 5321-5331 (2010).
61. Hirsch, V., et al. Surface charge of polymer coated SPIONs influences the serum protein adsorption, colloidal stability and subsequent cell interaction in vitro. Nanoscale 5, 3723-3732 (2013).
62. Praetner, M., et al. The contribution of the capillary endothelium to blood clearance and tissue deposition of anionic quantum dots in vivo. Biomaterials 31, 6692-6700 (2010).
63. Levchenko, T. S., Rammohan, R., Lukyanov, A. N., Whiteman, K. R. & Torchilin, V. P. Liposome clearance in mice: the effect of a separate and combined presence of surface charge and polymer coating. Int J Pharm 240, 95-102 (2002).
64. Sharma, B., Peetla, C., Adjei, I. M. & Labhasetwar, V. Selective biophysical interactions of surface modified nanoparticles with cancer cell lipids improve tumor targeting and gene therapy. Cancer Lett 334, 228-236 (2013).
65. Adjei, I. M., Peetla, C. & Labhasetwar, V. Heterogeneity in nanoparticles influences biodistribution and targeting. Nanomedicine (Lond) 9, 267-278 (2014).
66. Panyam, J. & Labhasetwar, V. Dynamics of endocytosis and exocytosis of poly(D,L-lactide-coglycolide) nanoparticles in vascular smooth muscle cells. Pharm Res 20, 212-220 (2003).
67. Panyam, J. & Labhasetwar, V. Sustained cytoplasmic delivery of drugs with intracellular receptors using biodegradable nanoparticles. Mol Pharm 1, 77-84 (2004).
68. Panyam, J., Zhou, W. Z., Prabha, S., Sahoo, S. K. & Labhasetwar, V. Rapid endo-lysosomal escape of poly (DL-lactide-co-glycolide) nanoparticles: implications for drug and gene delivery. FASEB J 16, 1217-1226 (2002).
69. Sahoo, S. K., Panyam, J., Prabha, S. & Labhasetwar, V. Residual polyvinyl alcohol associated with poly (D,L-lactide-co-glycolide) nanoparticles affects their physical properties and cellular uptake. J Control Release 82, 105-114 (2002).
70. Sharma, B., Peetla, C., Adjei, I. M. & Labhasetwar, V. Selective biophysical interactions of surface modified nanoparticles with cancer cell lipids improve tumor targeting and gene therapy. Cancer Lett 334, 228-236 (2013).
71. Panyam, J., et al. Polymer degradation and in vitro release of a model protein from poly(D,L-lactide-coglycolide) nano- and microparticles. J Control Release 92, 173-187 (2003).
72. Foy, S. P., et al. Optical imaging and magnetic field targeting of magnetic nanoparticles in tumors. ACS Nano 4, 5217-5224 (2010).
73. Suzuki, T., et al. Pattern of prostate cancer metastasis to the vertebral column. The Prostate 25, 141-146 (1994).
74. Mundy, G. R. Metastasis to bone: causes, consequences and therapeutic opportunities. Nat Rev Cancer 2, 584-593 (2002).
75. Park, S. I., Kim, S. J., McCauley, L. K. & Gallick, G. E. Preclinical mouse models of human prostate cancer and their utility in drug discovery. in Curr Protoc Pharmacol (John Wiley & Sons, Inc., 2001).
76. Nie, S., Hsiao, W. W., Pan, W. & Yang, Z. Thermoreversible Pluronic® F127-based hydrogel containing liposomes for the controlled delivery of paclitaxel: in vitro drug release, cell cytotoxicity, and uptake studies. Int J Nanomedicine 6, 151 (2011).
77. Vassileva, V., Allen, C. J. & Piquette-Miller, M. Effects of sustained and intermittent paclitaxel therapy on tumor repopulation in ovarian cancer. Mol Cancer Ther 7, 630-637 (2008).
78. Vassileva, V., et al. Efficacy assessment of sustained intraperitoneal paclitaxel therapy in a murine model of ovarian cancer using bioluminescent imaging. Br J Cancer 99, 2037-2043 (2008).
79. Desai, N., et al. Increased antitumor activity, intratumor paclitaxel concentrations, and endothelial cell transport of 79. cremophor-free, albumin-bound paclitaxel, ABI-007, compared with cremophor-based paclitaxel. Clin Cancer Res 12, 1317-1324 (2006).
80. Karapanagiotou, E. M., et al. Phase I/II trial of carboplatin and paclitaxel chemotherapy in combination with intravenous oncolytic reovirus in patients with advanced malignancies. Clin Cancer Res 18, 2080-2089 (2012).
81. Green, H., Khan, M. S., Jakobsen-Falk, I., Avall-Lundqvist, E. & Peterson, C. Impact of CYP3A5*3 and CYP2C8-HapC on paclitaxel/carboplatin-induced myelosuppression in patients with ovarian cancer. J Pharm Sci 100, 4205-4209 (2011).
82. Farokhzad, O. C., et al. Targeted nanoparticle-aptamer bioconjugates for cancer chemotherapy in vivo. Proc Natl Acad Sci USA 103, 6315-6320 (2006).
83. Kalaria, D. R., Sharma, G., Beniwal, V. & Ravi Kumar, M. N. Design of biodegradable nanoparticles for oral delivery of doxorubicin: in vivo pharmacokinetics and toxicity studies in rats. Pharma Res 26, 492-501 (2009).
84. Wang, N., et al. Prostate cancer cells preferentially home to osteoblast-rich areas in the early stages of bone metastasis—evidence from in vivo models. J Bone Miner Res (2014).
85. Owens, D. E., 3rd & Peppas, N. A. Opsonization, biodistribution, and pharmacokinetics of polymeric nanoparticles. Int J Pharm 307, 93-102 (2006).
86. Kakinoki, A., Kaneo, Y., Tanaka, T. & Hosokawa, Y. Synthesis and evaluation of water-soluble poly(vinyl alcohol)-paclitaxel conjugate as a macromolecular prodrug. Biol Pharm Bull 31, 963-969 (2008).
87. Tabata, Y., Murakami, Y. & Ikada, Y. Tumor accumulation of poly(vinyl alcohol) of different sizes after intravenous injection. J Control Release 50, 123-133 (1998).
88. Yamaoka, T., Tabata, Y. & Ikada, Y. Comparison of body distribution of poly(vinyl alcohol) with other water-soluble polymers after intravenous administration. J Pharm Pharmacol 47, 479-486 (1995).
89. Davda, J. & Labhasetwar, V. Characterization of nanoparticle uptake by endothelial cells. Int J Pharm 233, 51-59 (2002).
90. Qaddoumi, M. G., et al. Clathrin and caveolin-1 expression in primary pigmented rabbit conjunctival epithelial cells: role in PLGA nanoparticle endocytosis. Mol Vis 9, 559-568 (2003).
91. Maeda, H. The enhanced permeability and retention (EPR) effect in tumor vasculature: the key role of tumor-selective macromolecular drug targeting. Adv Enzyme Regul 41, 189-207 (2001).
92. Wolfram, J., et al. The nano-plasma interface: Implications of the protein corona. Colloids Surf B Biointerfaces (2014).
93. Lundqvist, M., et al. The Evolution of the Protein Corona around Nanoparticles: A Test Study. ACS Nano 5, 7503-7509 (2011).
94. Lynch, I. & Dawson, K. A. Protein-nanoparticle interactions. Nano Today 3, 40-47 (2008).
95. Jain, T. K., Reddy, M. K., Morales, M. A., Leslie-Pelecky, D. L. & Labhasetwar, V. Biodistribution, clearance, and biocompatibility of iron oxide magnetic nanoparticles in rats. Mol Pharm 5, 316-327 (2008).
96. Souris, J. S., et al. Surface charge-mediated rapid hepatobiliary excretion of mesoporous silica nanoparticles. Biomaterials 31, 5564-5574 (2010).
97. Kahn, D., et al. Positron emission tomographic measurement of bone marrow blood flow to the pelvis and lumbar vertebrae in young normal adults [published erratum appears in Blood 1994 Nov. 15; 84(10):3602]. Blood 83, 958-963 (1994).
98. Song, C. X., Labhasetwar, V. & Levy, R. J. Controlled release of U-86983 from double-layer biodegradable matrices: effect of additives on release mechanism and kinetics. J Control Release 45, 177-192 (1997).
99. Liu, Y. & Schwendeman, S. P. Mapping microclimate pH distribution inside protein-encapsulated PLGA microspheres using confocal laser scanning microscopy. Mol Pharm 9, 1342-1350 (2012).
100. Reddy, M. K. & Labhasetwar, V. Nanoparticle-mediated delivery of superoxide dismutase to the brain: an effective strategy to reduce ischemia-reperfusion injury. The FASEB Journal 23, 1384-1395 (2009).
101. Davda, J. & Labhasetwar, V. Sustained proangiogenic activity of vascular endothelial growth factor following encapsulation in nanoparticles. Journal of Biomedical Nanotechnology 1, 74-82 (2005).
102. Pourvasei, R., et al. Specific method validation and sample analysis approaches for biocomparability studies of denosumab addressing method and manufacture site changes. AAPS J 15, 70-77 (2013).
103. Bradley, E. W. & Oursler, M. J. Osteoclast culture and resorption assays. Methods Mol Biol 455, 19-35 (2008).
104. Shin, J.-W., Seol, I.-C. & Son, C.-G. Interpretation of Animal Dose and Human Equivalent Dose for Drug Development. The Journal of Korean Oriental Medicine 31, 1-7 (2010).
105. Kostenuik, P. J., et al. Denosumab, a fully human monoclonal antibody to RANKL, inhibits bone resorption and increases BMD in knock-in mice that express chimeric (murine/human) RANKL. J Bone Miner Res 24, 182-195 (2009).

All publications and patents mentioned in the specification and/or listed below are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope described herein.

We claim:

1. A method of treating cancer comprising: intravenously administering a composition to a subject,
   wherein said composition comprises nanoparticles encapsulating and/or conjugated to docetaxel,
   wherein said nanoparticles comprise:
   i) poly (D,L-lactide-co-glycolide) (PLGA),
   ii) a surface polymer comprising poly (vinyl alcohol) (PVA), and
   iii) a pore-forming agent;
   wherein said nanoparticles are non-PEGylated, are neutral or nearly neutral in charge, and where at least some of said nanoparticles have a diameter greater than about 75 nm but smaller than 170 nm,
   wherein said subject has cancer cells in at least one bone, wherein said cancer cells have metastasized to said at least one bone from another part of said subject, and
   wherein said administering kills at least some of said cancer cells in said at least one bone.

2. The method of claim 1, wherein said nanoparticles have a zeta potential between −5 and +5 mV.

3. The method of claim 1, wherein said nanoparticles have a zeta potential between −3 and +3 mV.

4. The method of claim 1, wherein said cancer cells are prostate cancer cells.

5. The method of claim 1, wherein said pore-forming agent comprises dimethyl tartaric acid (DMTA).

6. The method of claim 1, wherein said nanoparticles further encapsulate and/or are conjugated to an anti-RANKL antibody or binding fragment thereof.

* * * * *